US009267937B2

(12) United States Patent
Farokhzad et al.

(10) Patent No.: US 9,267,937 B2
(45) Date of Patent: Feb. 23, 2016

(54) SYSTEM FOR SCREENING PARTICLES

(75) Inventors: Omid C. Farokhzad, Chestnut Hill, MA (US); Aleksandar Filip Radovic-Moreno, State College, PA (US); Robert S. Langer, Newton, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 1443 days.

(21) Appl. No.: 12/097,118

(22) PCT Filed: Dec. 15, 2006

(86) PCT No.: PCT/US2006/047975
§ 371 (c)(1),
(2), (4) Date: Feb. 27, 2009

(87) PCT Pub. No.: WO2007/070682
PCT Pub. Date: Jun. 21, 2007

(65) Prior Publication Data
US 2009/0298710 A1 Dec. 3, 2009

Related U.S. Application Data

(60) Provisional application No. 60/750,765, filed on Dec. 15, 2005, provisional application No. 60/747,240, filed on May 15, 2006.

(51) Int. Cl.
*C40B 30/06* (2006.01)
*G01N 33/50* (2006.01)
(Continued)

(52) U.S. Cl.
CPC .............. *G01N 33/5088* (2013.01); *B82Y 5/00* (2013.01); *B82Y 15/00* (2013.01); *C40B 30/06* (2013.01); *A61K 47/4813* (2013.01); *A61K 47/48346* (2013.01); *A61K 47/48723* (2013.01)

(58) Field of Classification Search
CPC .......... G01N 33/5082; G01N 33/5085; G01N 33/5088; A61K 47/48346; A61K 47/48723; A61K 47/4813; B82Y 5/00; B82Y 15/00; C40B 30/06
USPC .......................................................... 506/10
See application file for complete search history.

(56) References Cited

U.S. PATENT DOCUMENTS 3,766,774 A 10/1973 Clark
4,270,537 A 6/1981 Romaine
(Continued)

FOREIGN PATENT DOCUMENTS

CA 2453959 1/2003
CA 2649149 10/2007
(Continued)

OTHER PUBLICATIONS

Anderson et al. (Advanced Drug Delivery Reviews, 1997, 28:5-24).*
(Continued)

*Primary Examiner* — Jeremy C Flinders
(74) *Attorney, Agent, or Firm* — Pabst Patent Group LLP

(57) ABSTRACT

Screening of a library of particles in vivo and/or in vitro using Polyplex Iterative Combinatorial Optimization (PICO) allows for the design of particles for targeting a specific organ, tissue (e.g., cancer), or cell. Particles may, for example, include different targeting agents (e.g., aptamers or plurality of aptamers) on their surfaces, and the aptamer or aptamers may be evolved to provide better targeting of the particles. Libraries of particles are enriched in characteristics of particles that have been found to migrate to a tissue of interest, be taken up by cells, etc. The process may be repeated to engineer particles of a desired specificity or biological function.

12 Claims, 5 Drawing Sheets

An example of polymer library complexity.

(51) Int. Cl.
  *B82Y 5/00*     (2011.01)
  *B82Y 15/00*    (2011.01)
  *A61K 47/48*    (2006.01)

(56) References Cited

U.S. PATENT DOCUMENTS

| | | | |
|---|---|---|---|
| 4,446,122 A | 5/1984 | Chu et al. |
| 4,596,556 A | 6/1986 | Morrow et al. |
| 4,631,211 A | 12/1986 | Houghten |
| 4,638,045 A | 1/1987 | Kohn et al. |
| 4,790,824 A | 12/1988 | Morrow et al. |
| 4,795,436 A | 1/1989 | Robinson |
| 4,806,621 A | 2/1989 | Kohn et al. |
| 4,818,542 A | 4/1989 | DeLuca |
| 4,839,416 A | 6/1989 | Orenstein |
| 4,862,851 A | 9/1989 | Washino et al. |
| 4,886,499 A | 12/1989 | Cirelli et al. |
| 4,902,615 A | 2/1990 | Freeman et al. |
| 4,904,479 A | 2/1990 | Illum |
| 4,940,460 A | 7/1990 | Casey, I et al. |
| 4,941,880 A | 7/1990 | Burns |
| 4,946,929 A | 8/1990 | D'Amore et al. |
| 4,959,219 A | 9/1990 | Chow |
| RE33,405 E | 10/1990 | Chu et al. |
| 4,970,299 A | 11/1990 | Bazinet et al. |
| 4,976,968 A | 12/1990 | Steiner |
| 5,010,167 A | 4/1991 | Ron et al. |
| 5,015,235 A | 5/1991 | Crossman |
| 5,019,379 A | 5/1991 | Domb et al. |
| 5,055,404 A | 10/1991 | Ueda et al. |
| 5,064,413 A | 11/1991 | McKinnon et al. |
| 5,069,936 A | 12/1991 | Yen |
| 5,093,246 A | 3/1992 | Cech et al. |
| 5,118,528 A | 6/1992 | Fessi et al. |
| 5,141,496 A | 8/1992 | Dalto et al. |
| 5,162,504 A | 11/1992 | Horoszewicz |
| 5,174,930 A | 12/1992 | Stainmesse |
| 5,175,296 A | 12/1992 | Gerster |
| 5,190,521 A | 3/1993 | Hubbard et al. |
| 5,200,181 A | 4/1993 | Soltys |
| 5,240,963 A | 8/1993 | Domb |
| 5,270,163 A | 12/1993 | Gold et al. |
| 5,312,335 A | 5/1994 | McKinnon et al. |
| 5,328,483 A | 7/1994 | Jacoby |
| 5,334,144 A | 8/1994 | Alchas et al. |
| 5,334,497 A | 8/1994 | Inaba et al. |
| 5,339,163 A | 8/1994 | Homma et al. |
| 5,342,781 A | 8/1994 | Su |
| 5,383,851 A | 1/1995 | McKinnon, Jr. et al. |
| 5,389,640 A | 2/1995 | Gerster |
| 5,399,665 A | 3/1995 | Barrera et al. |
| 5,403,750 A | 4/1995 | Braatz |
| 5,417,662 A | 5/1995 | Hjertman et al. |
| 5,449,513 A | 9/1995 | Yokoyama |
| 5,466,220 A | 11/1995 | Brenneman |
| 5,472,704 A | 12/1995 | Santus et al. |
| 5,480,381 A | 1/1996 | Weston |
| 5,500,161 A | 3/1996 | Andrianov et al. |
| 5,503,627 A | 4/1996 | McKinnon et al. |
| 5,512,600 A | 4/1996 | Mikos et al. |
| 5,514,378 A | 5/1996 | Mikos et al. |
| 5,520,639 A | 5/1996 | Peterson et al. |
| 5,527,288 A | 6/1996 | Gross et al. |
| 5,543,158 A | 8/1996 | Gref et al. |
| 5,567,588 A | 10/1996 | Gold et al. |
| 5,569,189 A | 10/1996 | Parsons |
| 5,578,325 A | 11/1996 | Domb et al. |
| 5,595,877 A | 1/1997 | Gold et al. |
| 5,599,302 A | 2/1997 | Lilley et al. |
| 5,622,699 A * | 4/1997 | Ruoslahti et al. ............... 506/9 |
| 5,649,912 A | 7/1997 | Peterson |
| 5,660,985 A | 8/1997 | Pieken et al. |
| 5,686,113 A | 11/1997 | Speaker |
| 5,696,175 A | 12/1997 | Mikos et al. |
| 5,696,249 A | 12/1997 | Gold et al. |
| 5,704,911 A | 1/1998 | Parsons |
| 5,716,404 A | 2/1998 | Vacanti et al. |
| 5,733,925 A | 3/1998 | Kunz et al. |
| 5,736,372 A | 4/1998 | Vacanti et al. |
| 5,744,155 A | 4/1998 | Friedman |
| 5,763,177 A | 6/1998 | Gold et al. |
| 5,766,635 A | 6/1998 | Spenleuhauer |
| 5,770,417 A | 6/1998 | Vacanti et al. |
| 5,786,204 A | 7/1998 | He et al. |
| 5,789,163 A | 8/1998 | Drolet et al. |
| 5,804,178 A | 9/1998 | Vacanti et al. |
| 5,817,785 A | 10/1998 | Gold et al. |
| 5,820,879 A | 10/1998 | Fernandez et al. |
| 5,837,752 A | 11/1998 | Shastri et al. |
| 5,843,653 A | 12/1998 | Gold et al. |
| 5,843,732 A | 12/1998 | Davis et al. |
| 5,853,984 A | 12/1998 | Davis et al. |
| 5,869,103 A | 2/1999 | Yah et al. |
| 5,871,747 A | 2/1999 | GengouxSedlik |
| 5,874,218 A | 2/1999 | Drolet et al. |
| 5,876,727 A | 3/1999 | Swain |
| 5,879,712 A | 3/1999 | Bomberger |
| 5,893,397 A | 4/1999 | Peterson et al. |
| 5,898,031 A | 4/1999 | Crooke |
| 5,902,599 A | 5/1999 | Anseth et al. |
| 5,916,539 A | 6/1999 | Pilgrimm |
| 5,928,647 A | 7/1999 | Rock |
| 5,942,252 A | 8/1999 | Tice |
| 5,958,691 A | 9/1999 | Pieken et al. |
| 5,977,089 A | 11/1999 | Arimilli et al. |
| 5,993,412 A | 11/1999 | Deily et al. |
| 6,001,577 A | 12/1999 | Gold et al. |
| 6,005,087 A | 12/1999 | Cook et al. |
| 6,007,845 A | 12/1999 | Domb et al. |
| 6,030,613 A | 2/2000 | Blumberg |
| 6,031,086 A | 2/2000 | Switzer |
| 6,039,969 A | 3/2000 | Tomai |
| 6,043,224 A | 3/2000 | Lee |
| 6,060,306 A | 5/2000 | Flatt |
| 6,083,505 A | 7/2000 | Miller |
| 6,095,148 A | 8/2000 | Shastri et al. |
| 6,107,094 A | 8/2000 | Crooke |
| 6,110,462 A | 8/2000 | Barbas et al. |
| 6,120,666 A | 9/2000 | Jacobson |
| 6,123,727 A | 9/2000 | Vacanti et al. |
| 6,127,533 A | 10/2000 | Cook et al. |
| 6,139,870 A | 10/2000 | Verrecchia |
| 6,184,364 B1 | 2/2001 | Pieken et al. |
| 6,190,913 B1 | 2/2001 | Singh |
| 6,197,346 B1 | 3/2001 | Mathiowitz |
| 6,225,460 B1 | 5/2001 | Bischofberger et al. |
| 6,232,082 B1 | 5/2001 | Ennifar |
| 6,235,313 B1 | 5/2001 | Mathiowitz |
| 6,238,705 B1 | 5/2001 | Liu et al. |
| 6,242,246 B1 | 6/2001 | Gold et al. |
| 6,245,776 B1 | 6/2001 | Skwierczynski |
| 6,254,890 B1 | 7/2001 | Hirosue et al. |
| 6,265,608 B1 | 7/2001 | Sumner, Jr. |
| 6,288,040 B1 | 9/2001 | Muller |
| 6,291,673 B1 | 9/2001 | Fuchs |
| 6,344,318 B1 | 2/2002 | Gold et al. |
| 6,348,462 B1 | 2/2002 | Gerster |
| 6,365,187 B2 | 4/2002 | Mathiowitz et al. |
| 6,376,190 B1 | 4/2002 | Gold et al. |
| 6,395,718 B1 | 5/2002 | Slusher |
| 6,399,754 B1 | 6/2002 | Cook |
| 6,403,779 B1 | 6/2002 | Kawasaki et al. |
| 6,429,200 B1 | 8/2002 | Monahan et al. |
| 6,444,782 B1 | 9/2002 | Hamlin |
| 6,451,527 B1 | 9/2002 | Larocca et al. |
| 6,458,539 B1 | 10/2002 | Gold et al. |
| 6,458,543 B1 | 10/2002 | Gold et al. |
| 6,482,594 B2 | 11/2002 | Gold et al. |
| 6,492,554 B2 | 12/2002 | Dalton et al. |
| 6,506,559 B1 | 1/2003 | Fire et al. |
| 6,506,577 B1 | 1/2003 | Deming et al. |
| 6,528,499 B1 | 3/2003 | Kozikowski |
| 6,558,951 B1 | 5/2003 | Tomai |
| 6,569,896 B2 | 5/2003 | Dalton et al. |

(56) References Cited

U.S. PATENT DOCUMENTS

| | | |
|---|---|---|
| 6,589,562 B1 | 7/2003 | Shefer et al. |
| 6,589,563 B2 | 7/2003 | Prokop |
| 6,608,201 B2 | 8/2003 | Gerster |
| 6,610,319 B2 | 8/2003 | Tomai |
| 6,610,713 B2 | 8/2003 | Tracey |
| 6,632,922 B1 | 10/2003 | Deming et al. |
| 6,656,469 B1 | 12/2003 | Svensson |
| 6,686,446 B2 | 2/2004 | Deming et al. |
| 6,686,472 B2 | 2/2004 | Gerster |
| 6,696,076 B2 | 2/2004 | Tomai |
| 6,699,474 B1 | 3/2004 | Cerny |
| 6,716,583 B2 | 4/2004 | Gold et al. |
| 6,723,429 B2 | 4/2004 | Bengs |
| 6,737,056 B1 | 5/2004 | Presta |
| 6,747,156 B2 | 6/2004 | Johansson |
| 6,767,702 B2 | 7/2004 | Mirkin |
| 6,818,732 B2 | 11/2004 | Deming et al. |
| 6,838,484 B2 | 1/2005 | Steiner et al. |
| 6,875,605 B1 | 4/2005 | Ma |
| 6,875,886 B2 | 4/2005 | Frangioni |
| 6,902,743 B1 | 6/2005 | Setterstrom |
| 6,932,971 B2 | 8/2005 | Bachmann et al. |
| 6,984,393 B2 | 1/2006 | Amsden |
| 6,995,284 B2 | 2/2006 | Dalton et al. |
| 6,998,500 B2 | 2/2006 | Dalton et al. |
| 7,008,411 B1 | 3/2006 | Mandrusov et al. |
| 7,022,870 B2 | 4/2006 | Dalton et al. |
| 7,026,500 B2 | 4/2006 | Dalton et al. |
| 7,029,859 B2 | 4/2006 | Thompson |
| 7,030,228 B1 | 4/2006 | Schmitz |
| 7,056,704 B2 | 6/2006 | Tuschl et al. |
| 7,078,196 B2 | 7/2006 | Tuschl et al. |
| 7,097,837 B2 | 8/2006 | Nielsen |
| 7,149,574 B2 | 12/2006 | Yun |
| 7,163,680 B2 | 1/2007 | Bander |
| 7,247,502 B2 | 7/2007 | Ennifar |
| 7,250,499 B2 | 7/2007 | Mirkin |
| 7,335,744 B2 | 2/2008 | Liu |
| 7,363,076 B2 | 4/2008 | Yun |
| 7,375,180 B2 | 5/2008 | Gorden |
| 7,387,271 B2 | 6/2008 | Noelle |
| 7,422,902 B1 | 9/2008 | Wheeler |
| 7,427,629 B2 | 9/2008 | Kedl |
| 7,488,792 B2 | 2/2009 | Ruoslahti |
| 7,550,441 B2 | 6/2009 | Farokhzad et al. |
| 7,727,969 B2 | 6/2010 | Farokhzad |
| 7,762,803 B2 | 7/2010 | Nakazato |
| 7,767,803 B2 | 8/2010 | Diener |
| 8,277,812 B2 | 10/2012 | Iannacone |
| 8,323,698 B2 | 12/2012 | Gu |
| 8,343,497 B2 | 1/2013 | Shi |
| 8,343,498 B2 | 1/2013 | Alexis |
| 8,562,998 B2 | 10/2013 | Shi |
| 8,574,564 B2 | 11/2013 | Renner |
| 8,637,028 B2 | 1/2014 | Alexis |
| 2001/0012890 A1 | 8/2001 | Thompson |
| 2002/0009466 A1 | 1/2002 | Brayden |
| 2002/0064780 A1 | 5/2002 | Gold et al. |
| 2002/0068091 A1 | 6/2002 | Davis et al. |
| 2002/0086356 A1 | 7/2002 | Tuschl et al. |
| 2002/0099036 A1 | 7/2002 | Dalton et al. |
| 2002/0099096 A1 | 7/2002 | Dalton et al. |
| 2002/0102613 A1 | 8/2002 | Hogenboom |
| 2002/0106647 A1 | 8/2002 | Segal |
| 2002/0116054 A1 | 8/2002 | Lundell |
| 2002/0119473 A1 | 8/2002 | Lupold |
| 2002/0119916 A1 | 8/2002 | Hassan |
| 2002/0150578 A1 | 10/2002 | He et al. |
| 2002/0151004 A1 | 10/2002 | Craig |
| 2002/0153251 A1 | 10/2002 | Sassi et al. |
| 2002/0156125 A1 | 10/2002 | Broder et al. |
| 2002/0173495 A1 | 11/2002 | Dalton et al. |
| 2003/0003103 A1 | 1/2003 | Thompson |
| 2003/0003114 A1 | 1/2003 | Pan |
| 2003/0009029 A1 | 1/2003 | Buchholz et al. |
| 2003/0022868 A1 | 1/2003 | Dalton et al. |
| 2003/0035804 A1 | 2/2003 | D'Amico et al. |
| 2003/0054360 A1 | 3/2003 | Gold et al. |
| 2003/0087301 A1 | 5/2003 | Smith et al. |
| 2003/0099668 A1 | 5/2003 | Bachmann |
| 2003/0108611 A1 | 6/2003 | Bosch et al. |
| 2003/0108923 A1 | 6/2003 | Tuschl et al. |
| 2003/0133988 A1 | 7/2003 | Fearon |
| 2003/0134810 A1 | 7/2003 | Springate et al. |
| 2003/0138557 A1 | 7/2003 | Allison |
| 2003/0143184 A1 | 7/2003 | Seo |
| 2003/0162761 A1 | 8/2003 | Steiner et al. |
| 2003/0165478 A1 | 9/2003 | Sokoll |
| 2003/0175950 A1 | 9/2003 | McSwiggen |
| 2003/0219766 A1 | 11/2003 | Raitano et al. |
| 2003/0225040 A1 | 12/2003 | Dalton et al. |
| 2003/0228603 A1 | 12/2003 | Cload |
| 2003/0232013 A1 | 12/2003 | Sieckman et al. |
| 2003/0232792 A1 | 12/2003 | Dalton et al. |
| 2003/0235619 A1 | 12/2003 | Allen |
| 2004/0014789 A1 | 1/2004 | Lau |
| 2004/0014975 A1 | 1/2004 | Dalton et al. |
| 2004/0022727 A1 | 2/2004 | Stanton |
| 2004/0022840 A1 | 2/2004 | Nagy et al. |
| 2004/0029913 A1 | 2/2004 | Dalton et al. |
| 2004/0043923 A1 | 3/2004 | Parma et al. |
| 2004/0052727 A1 | 3/2004 | Dalton et al. |
| 2004/0054190 A1 | 3/2004 | Pomper |
| 2004/0059094 A1 | 3/2004 | Bachmann et al. |
| 2004/0067196 A1 | 4/2004 | Brunke et al. |
| 2004/0067503 A1 | 4/2004 | Tan et al. |
| 2004/0067979 A1 | 4/2004 | Dalton et al. |
| 2004/0072234 A1 | 4/2004 | Parma et al. |
| 2004/0086544 A1 | 5/2004 | Bezemer |
| 2004/0087810 A1 | 5/2004 | Dalton et al. |
| 2004/0092470 A1 | 5/2004 | Leonard et al. |
| 2004/0136961 A1 | 7/2004 | Prokop et al. |
| 2004/0141958 A1 | 7/2004 | Steinaa |
| 2004/0147489 A1 | 7/2004 | Dalton et al. |
| 2004/0147550 A1 | 7/2004 | Dalton et al. |
| 2004/0156846 A1 | 8/2004 | Daum et al. |
| 2004/0167103 A1 | 8/2004 | Dalton et al. |
| 2004/0192626 A1 | 9/2004 | McSwiggen et al. |
| 2004/0241790 A1 | 12/2004 | Eriksen et al. |
| 2004/0247680 A1 | 12/2004 | Farokhzad |
| 2004/0248088 A1 | 12/2004 | Raitano et al. |
| 2004/0260092 A1 | 12/2004 | Miller et al. |
| 2004/0260108 A1 | 12/2004 | Dalton et al. |
| 2004/0266688 A1 | 12/2004 | Nayak |
| 2005/0017667 A1 | 1/2005 | Yamamoto |
| 2005/0019870 A1 | 1/2005 | Afar et al. |
| 2005/0019872 A1 | 1/2005 | Afar et al. |
| 2005/0020525 A1 | 1/2005 | McSwiggen et al. |
| 2005/0032733 A1 | 2/2005 | McSwiggen et al. |
| 2005/0033074 A1 | 2/2005 | Dalton et al. |
| 2005/0037075 A1* | 2/2005 | Farokhzad et al. ........... 424/468 |
| 2005/0048063 A1 | 3/2005 | Ruoslahti et al. |
| 2005/0069910 A1 | 3/2005 | Turner et al. |
| 2005/0079152 A1 | 4/2005 | Bot |
| 2005/0079553 A1 | 4/2005 | Ayyoub |
| 2005/0080128 A1 | 4/2005 | Tsukamoto et al. |
| 2005/0100877 A1 | 5/2005 | Xu et al. |
| 2005/0107322 A1 | 5/2005 | OHagan |
| 2005/0122550 A1 | 6/2005 | Plewa et al. |
| 2005/0136258 A1 | 6/2005 | Nie |
| 2005/0142582 A1 | 6/2005 | Doyle |
| 2005/0158390 A1 | 7/2005 | Rana et al. |
| 2005/0191294 A1 | 9/2005 | Arap et al. |
| 2005/0207940 A1 | 9/2005 | Butler |
| 2005/0214378 A1 | 9/2005 | Hoarau |
| 2005/0233948 A1 | 10/2005 | D'Amico et al. |
| 2005/0239134 A1 | 10/2005 | Gorenstein |
| 2005/0244863 A1 | 11/2005 | Mir |
| 2005/0249799 A1 | 11/2005 | Jacob et al. |
| 2005/0256071 A1 | 11/2005 | Davis |
| 2005/0260186 A1 | 11/2005 | Bookbinder et al. |
| 2006/0002852 A1 | 1/2006 | Saltzman et al. |
| 2006/0002971 A1 | 1/2006 | Saltzman |
| 2006/0004042 A1 | 1/2006 | Dalton et al. |

(56) References Cited

U.S. PATENT DOCUMENTS

| | | |
|---|---|---|
| 2006/0009529 A1 | 1/2006 | Dalton et al. |
| 2006/0035966 A1 | 2/2006 | Dalton et al. |
| 2006/0057219 A1 | 3/2006 | Nagasaki |
| 2006/0062787 A1 | 3/2006 | Hitraya |
| 2006/0083711 A1 | 4/2006 | Berry et al. |
| 2006/0110460 A1 | 5/2006 | Ferret |
| 2006/0111271 A1 | 5/2006 | Cerny |
| 2006/0165987 A1 | 7/2006 | Hildgen |
| 2006/0173170 A1 | 8/2006 | Chamberlian et al. |
| 2006/0183931 A1 | 8/2006 | Dalton et al. |
| 2006/0228371 A1 | 10/2006 | Raso |
| 2006/0239907 A1 | 10/2006 | Luzzi et al. |
| 2006/0240093 A1 | 10/2006 | Maclachlan et al. |
| 2006/0241180 A1 | 10/2006 | Dalton et al. |
| 2006/0258628 A1 | 11/2006 | Steiner et al. |
| 2006/0269557 A1 | 11/2006 | Sherman et al. |
| 2006/0276540 A1 | 12/2006 | Dalton et al. |
| 2006/0287547 A1 | 12/2006 | Dalton et al. |
| 2007/0014807 A1 | 1/2007 | Maida |
| 2007/0041901 A1 | 2/2007 | Diener |
| 2007/0043066 A1 | 2/2007 | Sum |
| 2007/0053845 A1 | 3/2007 | Sengupta |
| 2007/0116768 A1 | 5/2007 | Chorny |
| 2007/0184068 A1 | 8/2007 | Renner |
| 2007/0224225 A1 | 9/2007 | IracheGarreta |
| 2007/0225213 A1 | 9/2007 | Kosak |
| 2008/0019908 A1 | 1/2008 | Akitsu |
| 2008/0026000 A1 | 1/2008 | Ennifar |
| 2008/0031899 A1 | 2/2008 | Reddy |
| 2008/0057102 A1 | 3/2008 | Roorda |
| 2008/0081074 A1 | 4/2008 | Gu et al. |
| 2008/0124400 A1 | 5/2008 | Liggins |
| 2008/0171059 A1 | 7/2008 | Howland |
| 2008/0193381 A1 | 8/2008 | Babich |
| 2008/0213377 A1 | 9/2008 | Bhatia |
| 2008/0268063 A1 | 10/2008 | Jon et al. |
| 2008/0299177 A1 | 12/2008 | Hardy |
| 2009/0004118 A1 | 1/2009 | Nie |
| 2009/0028910 A1 | 1/2009 | DeSimone et al. |
| 2009/0061010 A1 | 3/2009 | Zale |
| 2009/0074828 A1 | 3/2009 | Alexis |
| 2009/0117549 A1 | 5/2009 | Tan |
| 2009/0192100 A1 | 7/2009 | Vater |
| 2009/0298710 A1 | 12/2009 | Farokhzad |
| 2010/0022680 A1 | 1/2010 | Karnik et al. |
| 2010/0068285 A1 | 3/2010 | Zale |
| 2010/0068286 A1 | 3/2010 | Troiano |
| 2010/0069426 A1 | 3/2010 | Zale |
| 2010/0092425 A1 | 4/2010 | Von Andrian et al. |
| 2010/0104655 A1 | 4/2010 | Zale |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0183727 A1 | 7/2010 | Iannacone et al. |
| 2010/0196482 A1 | 8/2010 | Radovic-Moreno et al. |
| 2010/0203142 A1 | 8/2010 | Zhang et al. |
| 2010/0216804 A1 | 8/2010 | Zale |
| 2010/0226986 A1 | 9/2010 | Grayson |
| 2010/0233251 A1 | 9/2010 | Von Andrian et al. |
| 2010/0266491 A1 | 10/2010 | Farokhzad |
| 2010/0297233 A1 | 11/2010 | Moretti |
| 2010/0303723 A1 | 12/2010 | Farokhzad |
| 2011/0052697 A1 | 3/2011 | Farokhzad |

FOREIGN PATENT DOCUMENTS

| | | |
|---|---|---|
| DK | 0418187 | 3/1991 |
| EP | 0333523 | 9/1989 |
| EP | 1279404 | 1/2003 |
| EP | 1752141 | 2/2007 |
| EP | 1872793 | 1/2008 |
| EP | 1932538 | 6/2008 |
| EP | 2106806 | 10/2009 |
| JP | 2006528954 | 5/2006 |
| KR | 0418916 | 3/2002 |
| KR | 0041712 | 6/2004 |
| WO | WO 88/04300 | 6/1988 |
| WO | WO 90/11364 | 3/1990 |
| WO | 9006430 | 6/1990 |
| WO | 9006433 | 6/1990 |
| WO | 9106286 | 5/1991 |
| WO | 9106287 | 5/1991 |
| WO | 9503356 | 2/1995 |
| WO | 9503357 | 2/1995 |
| WO | WO 97/04747 | 2/1997 |
| WO | WO 97/13537 | 4/1997 |
| WO | WO 97/37705 | 10/1997 |
| WO | WO 98/08856 | 3/1998 |
| WO | 98/51325 | 11/1998 |
| WO | 99/01498 | 1/1999 |
| WO | WO 99/34850 | 7/1999 |
| WO | 9955715 | 11/1999 |
| WO | WO 00/21572 | 4/2000 |
| WO | WO 00/27363 | 5/2000 |
| WO | 0032239 | 6/2000 |
| WO | WO 00/44895 | 8/2000 |
| WO | 0059538 | 10/2000 |
| WO | WO 01/75164 | 10/2001 |
| WO | WO 02/18477 | 3/2002 |
| WO | WO 02/076469 | 10/2002 |
| WO | WO 02/076603 | 10/2002 |
| WO | WO 02/100442 | 12/2002 |
| WO | WO 03/000777 | 1/2003 |
| WO | WO 03/004654 | 1/2003 |
| WO | 03033592 | 4/2003 |
| WO | WO 03/028657 | 4/2003 |
| WO | WO 03/030941 | 4/2003 |
| WO | WO 03/051304 | 6/2003 |
| WO | 03074679 | 9/2003 |
| WO | WO 03/072637 | 9/2003 |
| WO | WO 03/102708 | 12/2003 |
| WO | 2004009116 | 1/2004 |
| WO | 2004030608 | 4/2004 |
| WO | WO 2004/030608 | 4/2004 |
| WO | WO 2004/071493 | 8/2004 |
| WO | 2004096140 | 11/2004 |
| WO | WO 2004/096998 | 11/2004 |
| WO | 2004105782 | 12/2004 |
| WO | WO 2005/012407 | 2/2005 |
| WO | WO 2005/028539 | 3/2005 |
| WO | 2005046572 | 5/2005 |
| WO | WO 2005/042573 | 5/2005 |
| WO | WO 2005/072710 | 8/2005 |
| WO | 2005105056 | 11/2005 |
| WO | WO 2005/111192 | 11/2005 |
| WO | 2005112885 | 12/2005 |
| WO | 2005112886 | 12/2005 |
| WO | WO 2005/121181 | 12/2005 |
| WO | 2006025627 | 3/2006 |
| WO | WO 2006/037979 | 4/2006 |
| WO | WO 2006/042146 | 4/2006 |
| WO | WO 2006/066158 | 6/2006 |
| WO | WO 2006/078278 | 7/2006 |
| WO | WO 2006/090924 | 8/2006 |
| WO | 2006093991 | 9/2006 |
| WO | 2006099445 | 9/2006 |
| WO | WO 2006/096754 | 9/2006 |
| WO | WO 2006/117217 | 11/2006 |
| WO | WO 2006/133271 | 12/2006 |
| WO | WO 2006/138463 | 12/2006 |
| WO | 2007001448 A2 | 1/2007 |
| WO | WO 2007/021142 | 2/2007 |
| WO | 2007024026 | 3/2007 |
| WO | 2007034479 | 3/2007 |
| WO | 2007052058 | 5/2007 |
| WO | WO 2007/070682 | 6/2007 |
| WO | WO 2007/076371 | 7/2007 |
| WO | WO 2007/084797 | 7/2007 |
| WO | 2007098254 | 8/2007 |
| WO | 2007098254 A2 | 8/2007 |
| WO | WO 2007/109364 | 9/2007 |
| WO | WO 2007/118653 | 10/2007 |
| WO | 2007131972 | 11/2007 |

(56) References Cited

FOREIGN PATENT DOCUMENTS

| WO | 2007133807 | 11/2007 |
|---|---|---|
| WO | 2007137117 | 11/2007 |
| WO | 2007144807 A2 | 12/2007 |
| WO | WO 2007/150030 | 12/2007 |
| WO | 2008019142 | 2/2008 |
| WO | 2008041703 | 4/2008 |
| WO | 2008043157 | 4/2008 |
| WO | 2008058192 | 5/2008 |
| WO | WO 2008/051291 | 5/2008 |
| WO | 2008105772 | 9/2008 |
| WO | 2008105773 | 9/2008 |
| WO | 2008121949 | 10/2008 |
| WO | 2008124632 | 10/2008 |
| WO | 2008124634 | 10/2008 |
| WO | 2008124639 | 10/2008 |
| WO | 2008147456 | 12/2008 |
| WO | WO 2009/051837 | 4/2009 |
| WO | WO 2009/109428 | 9/2009 |
| WO | 2010005721 | 1/2010 |
| WO | 2010005723 | 1/2010 |
| WO | 2010005725 | 1/2010 |
| WO | 2010005726 | 1/2010 |
| WO | 2010068866 | 6/2010 |
| WO | 2010075072 | 7/2010 |
| WO | 2010114768 | 10/2010 |
| WO | 2010114770 | 10/2010 |
| WO | 2011072218 | 6/2011 |

OTHER PUBLICATIONS

Fahmy et al. (Nano Today, Aug. 2005, pp. 18-26).*
Akerman et al. (Proc. Natl. Acad. Sci., 2002, 99(20):12617-12621).*
Yoo et al. (J. Control. Release, 2004, 96:273-283).*
Weissleder et al. (Nature Biotechnology, vol. 23, pp. 1418-1423, published onlne Oct. 23, 2005).*
Bies et al., Lectin-medicated drug targeting: history and applications, *Advanced Drug Delivery Reviews*, 56:425-435 (2004).
Bocca, et al., "Phagocytic uptake of fluorescent stealth solid lipid nanoparticles", *Int. J. Pharmaceutics*, 175:185-193 (1998).
Brooking et al., "Transport of Nanoparticles Across the Rat Nasal Mucosa", *Journal of Drug Targeting*, 9(4):267-279 (2001).
Chandy et al., "Development of Poly(Lactic Acid)/Chitosan Co-Matrix Microspheres: Controlled Release of Taxol-Heparin for Preventing Restenosis", *Drug Delivery*, 8:77-86 (2001).
Grandy, et al., "5-Fluorouracil-loaded chitosan coated polylactic acid pmicrospheres as biodegradable drug carriers for cerebral tumors", *J. Microencapsulation*, 17(5):625-638 (2000).
Cheng, et al., "Formulation of functionalized PLGA-PEG nanoparticles for in vivo targeted drug delivery", *Biomaterrials*, 28:869-875 (2007).
Coppi, et al., "Chitosan-Alginate Microparticles as a Protein Carrier", *Drug Development and Industrial Pharmacy*, 27(5):393-400 (2001).
Elvassore, et al., "Production iof Insulin-Loaded Poly(Ethylene Glycol)/Poly(/-Lactide) (PEG/PLA) Nanoparticles by Gas Antisolvent Techniques", *Journal of Pharmacrutical Sciences*, 90(10):1628-36 (2001).
Ermak and Giannasca, "Microparticle targeting to M cells", *Advanced Drug Delivery Reviews*, 34:261-283 (1998).
Fi Li Povic-Grcic et al., "Mucoadhesive chitosan-coated liposomes: characteristics and stability", *J. Microencapsulation*, 18 1:3-12 (2001).
Gaserod et al., "The enhancement of the bioadhesive properties of calcium alginate gel beads by coating with chitosan", *Intl. J. of Pharmaceutics*, 175:237-246 (1998).
Hejazi et al ., "Stomach-specific anti-H. pylon therapy. I: preparation and characterization of tetracyline-loaded chitosan microshperes", *Intl. J. of Pharmaceutics*, 235:87-94 (2002).
Huang et al., "Microencapsulation of Chlorpheniramine Maleate-Resin Particles with Crosslinked Chitosan for Sustained Release", *Pharmaceutical Development and Technology*, 4 1:107-115 (1999).

Janes et al., "Chitosan nanoparticles as delivery systems for doxorubicin", *Journal of Controlled Release*, 73:255-267 (2001).
Jayasena, "Aptamers: An Emerging Class of Molecules That Rival Antibodies in Diagnostics", *Clinical Chemistry*, 45(9):1628-1650 (1999).
Kawashima, et al., "Mucoadhesive DL-Lactide/Glycolide Copolymer Nanoshperes Coated with Chitosan to Improve Oral Delivery of Elcatonin", *Pharmaceutical Development and Technology*, 5(1):77-85 (2000).
Khandare, et al., "Polymer-drug conjugates: Progress in polymeric prodrugs," *Progress in Polymer Science*, 31(4): 359-397 (2006).
Kim, et al., "Target-specific cellular uptake of PLGA nanoparticles coated with poly(L-lysine)-poly(ethyleneglycol)-folate conjugate", *Langmuir*, 21(19): 8852-8857 (2005).
Lehr, "Lectin-mediated drug delivery: The second generation of bioadhesives", *J. of Controlled Release*, 65:19-29 (2000).
Lim et al., "Preparation and evaluation of the in vitro drug release properties and mucoadhesion of novel microspheres of hyaluronic acid and chitosan", *J. of Controlled Release*, 66:281-292 (2000).
Mi, et al., "Release of Indomethacin from a Novel Chitosan Microsphere Prepared by a Natrually Occurring Crosslinker: Examination of Crosslinking and Polycation-Anionic Drug Interaction", *J. of Applied Polymer Science*, 81:1700-1711 (2001).
Olivier, et al., "Drug Transport to Brain with Targeted Nanoparticles", *J. of the Am. Society of Experimental NeuroTherapeutics*, 2:108-119 (2005).
Pimentel, et al., "Peptide nanoparticles as novel immunogens: design and analysis of a prototypic severe acute respiratory syndrome vaccine", *Chemical Biology & Drug Design*, 73(1):53-61 (2009).
Ponchel, et al., "Specific and non-specific bioadhesive particulate systems for oral delivery to the gastrointestinal tract", *Advanced Drug Delivery Reviews*, 34:191-219 (1998).
Shimoda, et al., "Bioadhesive Characteristics of Chitosan Mircroshperes to the Mucosa of Rat Small Intestine", *Drug Delvelopment and Inustrial Pharmacy*, 27(6):567-576 (2001).
Simberg, et al., "Biomimetic amplification of nanoparticle homing to tumors", *Nat'l. Acad. Sic. USA*, 104(3):921-936 (2007).
Takeuchi, et al., "Enteral Absorption of Insulin in Rats from Mucoadhesive Chitosan-Coated Liposomes", *Pharmaceutical Research*, 13(6):896-901 (1996).
Takeuchi et al., "Mucoadhesive Lipsomes Coated with Chitosan or Carbopol for Oral Administration of Peptide Drugs", *Proceed. Intl. Symp. Control. Rel. Bioact. Mater.*, 26:988-989 (1999).
Takeuchi, et al., "Spray-Dried Lactose Composite Particles Containing an Ion Complex of Alginate-Chitosan for Desinging a Dry-Coated Tablet Having a Time-Controlled Releasing Function", *Pharmaceutical Research*, 17 (1):94-99 (2000).
Tavitian, et al., "In vivo imaging with oligonucleotides for diagnosis and drug development", *Gut, 52 Su*, I IV :40-47 (2003).
Tobio, et al "Role of PEG on the stability in digestive fluids and in vivo fate of PEG-PLA nanoparticles following oral administration", *Colloids and Surfaces B: Biainterferences*, 18:315-323 (2000).
Vila, et al., "Design of biodegradable particles for protein delivery", *Journal of Controlled Release*, 78:15-24 (2002).
Vila, et al., "PLA-PEG Nanospheres: New Carriers for Transmucosal Delivery of Proteins and Plasmid DNA", *Poly. Adv. Technol.*, 13:851-858 (2002).
Yamada, et al., "In Vitro and in Vivo Evaluation of Sustained Release Chitosan-Coat Ketoprofen Microparticles", *Yakugaku Zasshi*, 121(3):239-245 (2001).
Yourong, et al, "Preparation of DHAQ-loaded mPEG-PLGA-mPEG nanoparticles and evaluation of drug release behaviors in vitro/in vivo," *J. Mat. Sci.: Mat. Med.*, 17(6): 509-16 (2006).
Yuan, et al., "Intranasal immunization with chitosan/pCETP nanoparticles inhibits atherosclerosis in a rabbit model of atherosclerosis", *Vaccine, Bitterworth Scientific*, 26:29-30 (2008).
Heald, et al., "Poly(lactic acid)-poly(ethylene oxide) (PLA-PEG) nanoparticles: NMR studies of the central solidlike PLA core and the liquid PEG corona", *Langmuir*, 18:3669-3675 (2002).
Tomai, et al., "Resiquimod and other immune response modifiers as vaccine adjuvants", Expert Rev Vaccines, 6:835-847 (2007) Abstract Only.

(56) References Cited

OTHER PUBLICATIONS

Villa, et al., "PLA-PEG particles as nasal protein carriers: the influence of the particle size", *Int. J Pharmaceut.*, 292:43-52 (2005).
Sarkar, et al., "Ligand-DNA interaction in a nanocage of reverse micelle", Biopolymer., 83(6):675-86 (2006).
International Search report mailed Sep. 22, 2008.
U.S. Appl. No. 12/239,136, filed Sep. 26, 2008, Farokhzad, et al.
U.S. Appl. No. 12/301,225, filed Nov. 17, 2008, Farokhzad, et al.
U.S. Appl. No. 12/515,456, filed May 5, 2010, Farokhzad, et al.
U.S. Appl. No. 12/526,300, filed Aug. 11, 2010, Moretti, et al.
Abad, et al., "Comparison of a Monoclonal Antibody-Based Enzyme-Linked Immunosorbent Assay and Gas Chromatography for the Determination of Nicotine in Cigarette Smoke Condensates", *Anal. Chem.*, 65:3227-3231 (1993).
Ackermand & Cresswell, "Cellular mechanisms governing cross-presentation of exogenous antigens", *Nat. Immunol.*, 5(7):678-684 (2004).
Aime, et al., "Lanthanide(III) chelates for NMR biomedical applications", *Chemical Society Reviews*, 27:19-29 (1998).
Akaishi, et al., "Targeting Chemotherapy Using Antibody-Combined Liposome against Human Pancreatic Cancer Cell-Line", *Tohoku J. Exp. Med.*, 175(1):29-42 (1995).
Allen, et al., "Nano-engineering block copolymer aggregates for drug delivery.", *Colloids Surfaces B—Biointerfaces*, 16:3-27 (1999).
Allison, et al., "The mode of action of immunological adjuvants.", *Dev. Biol. Stand.*, 92:3-11 (1998).
Altschul, et al., "Basic local alignment search tool.", *J. Mol. Biol.*, 215(3):403-10 (1990).
Altschul, et al., "Gapped BLAST and PSI-BLAST: a new generation of protein database search programs.", *Nucleic Acids Res.*, 25(17):3389-3402 (1997).
Angelucci, et al., "Neuroendocrine transdifferentiation induced by VPA is mediated by PPAR activation and confers resistance to antiblastic therapy in prostate carcinoma", *The Prostate*, 68(6):588-598 (2008).
Atkinson, et al., "Conjugation of folate via gelonin carbohydrate residues retains ribosomal-inactivating properties of the toxin and permits targeting to folate receptor positive cells.", *J. Biol. Chem.*, 276(30):27930-27935 (2001).
Baba, et al., "Human neutralizing monoclonal antibodies of the IgG1 subtype protect against mucosal simian-human immunodeficiency virus infection.", *Nat. Med.*, 6(2):200-206 (2000).
Babaian, et al., "Radioimmunological imaging of metastatic prostatic cancer with 111indium-labeled monoclonal antibody PAY 276.", *J. Urol.*, 137(3):439-443 (1987).
Bachmann, et al., "T helper cell-independent neutralizing B cell response against vesicular stomatitis virus: role of antigen patterns in B cell induction?", *Eur. J. Immunol.*, 25(12):3445-3451 (1995).
Bagalkot, et al., "An Aptamer-Doxorubicin Physical Conjugate as a Novel Targeted Drug-Delivery Platform", *Angew. Chem. Int. Ed.*, 45(48):8149-8152 (2006).
Bander, et al., "Targeting metastatic prostate cancer with radiolabeled monoclonal antibody J591 to the extracellular domain of prostate specific membrane antigen.", *J. Urol.*, 170(5):1717-1721 (2003).
Barchet, et al., "Virus-induced interferon alpha production by a dendritic cell subset in the absence of feedback signaling in vivo.", *J. Exp. Med.*, 195(4):507-516 (2002).
Barrera, et al., "Synthesis and RGD peptide modification of a new biodegradable copolymer: poly(lactic acid-co-lysine)", *J. Am. Chem. Soc.*, 115(23):11010-11011 (1993).
Bauer, et al., "SMS 201-995: a very potent and selective octapeptide analogue of somatostatin with prolonged action.", *Life Sci.*, 31(11):1133-1140 (1982).
Beaureparie, et al., "Functionalized Fluorescent Oxide Nanoparticles: Artificial Toxins for Sodium Channel Targeting and Imaging at the Single-Molecule Level", *Nano Letters*, 4(11):2079-2083 (2004).

Bennett, et al., "Inhibition of the Aminopeptidase from Aeromonas Proteolytica by I-Leucinephosphonic Acid, a Transition State Analogue of Peptide Hydrolysis", *J. Am. Chem. Soc.*, 120(46):12139-12140 (1998).
Binetruy-Tournaire, et al., "Identification of a peptide blocking vascular endothelial growth factor (VEGF)-mediated angiogenesis.", *EMBO J.*, 19(7):1525-1533 (2000).
Bjerke, et al., "Comparison of monoclonal and polyclonal antibodies to continine in nonisotopic and isotopic immunoassays", *J. Immunol. Meth.*, 96:239-246 (1987).
Boes, et al., "T-cell engagement of dendritic cells rapidly rearranges MHC class II transport.", *Nature*, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8+ T cell tolerance.", *J. Exp. Med.*, 196(12):1627-1638 (2002).
Bottausci, et al., "Mixing in the shear superposition micromixer: three-dimensional analysis", *Philosophical Transactions of the Royal Society of London Series a—Mathematical Physical and Engineering Sciences*, 362:1001-1018 (2004).
Boussif, et al., "A versatile vector for gene and oligonucleotide transfer into cells in culture and in vivo: polyethylenimine.", *Proc. Natl. Acad. Sci., USA*, 1995, 92:7297-7301 (1995).
Bozzacco, et al., "DEC-205 receptor on dendritic cells mediates presentation of HIV gag protein to CD8+ T cells in a spectrum of human MHC I haplotypes.", *Proc. Natl. Acad. Sc., USA*, 104(4):1289-1294 (2007).
Brito, et al., "Nanoparticulate carriers for the treatment of coronary restenosis.", *Int J Nanomedicine*, 2(2):143-161 (2007).
Burmeister, et al., "Direct in vitro selection of a 2'-0-methyl aptamer to VEGF.", *Chem Biol*, 12(1):25-33 (2005).
Carino, et al., "Nanosphere based oral insulin delivery," *J. Control. Release*, 65(1-2):261-9 (2000).
Casola, et al., "B cell receptor signal strength determines B cell fate.", *Nat. Immunol.*, 5(3):317-327 (2004).
Castro & Prieto, "Nicotine Antibody Production: Comparison of two nicotine conjugates in different animal species", *Biochem. Biophys. Res. Comm.*, 67(2):583-589 (1975).
Castro, et al., "Nicotine Antibodies: Comparison of Ligand Specificities of Antibodies Produced against Two Nicotine Conjugates", *Eur. J. Biochem.*, 104:331-340 (1980).
Chacon, et al., "Optimized preparation of poly D,L (lactic-glycolic) microspheres and nanoparticles for oral administration", *Int'l J. Pharmaceutics*, 141:81-91 (1996).
Chaires, et al., "Preferential binding of daunomycin to 5'ATCG and 5'ATGC sequences revealed by footprinting titration experiments.", *Biochemistry*, 29(26):6145-6153 (1990).
Chang, et al., "Five Different Anti-Prostate-specific Membrane Antigen (PSMA) Antibodies Confirm PSMA Expression in Tumor-associated Neovasculature", *Cancer Res.*, 59:3192-3198 (1999).
Cheng, et al., "Formulation of functionalized PLGA-PEG nanoparticles for in vivo targeted drug delivery.", *Biomaterials*, 28(5):869-876 (2007).
Christian, et al., "Nucleolin expressed at the cell surface is a marker of endothelial cells in angiogenic blood vessels.", *J. Cell Biol.*, 163(4):871-878 (2003).
Chu, et al., "Aptamer mediated siRNA delivery", *Nuc. Acid Res.*, 34:e73 (2006).
Chu, et al., "Labeling tumor cells with fluorescent nanocrystal-aptamer bioconjugates.", *Biosens. Bioelectron.*, 21:1859-1866 (2006).
Clark, "The reticulum of lymph nodes in mice studied with the electron microscope.", *Am. J. Anat.*, 110:217-257 (1962).
Connor, et al., "Ex vivo evaluation of anti-EpCAM immunocytokine huKS-IL2 in ovarian cancer.", *J. Immunother.*, 27(3):211-219 (2004).
Croy and Kwon, "Polymeric micells for drug delivery", *Curr. Pharm. Design*, 12:4669-4684 (2006).
D'Antonio, et al., "Longitudinal analysis of androgen deprivation of prostate cancer cells identifies pathways to androgen independence", *The Prostate*, 68(7):698-714 (2008).

(56) References Cited

OTHER PUBLICATIONS

Dang and Rock, "Stimulation of B lymphocytes through surface Ig receptors induces LFA-1 and ICAM-1-dependent adhesion.", *J. Immunol.*, 146(10):3273-3279 (1991).

De Graaf, et al., "A fully human anti-Ep-CAM scFv-beta-glucuronidase fusion protein for selective chemotherapy with a glucuronide prodrug.", *Br. J. Cancer*, 86(5):811-818 (2002).

De Jaeghere, et al., "Freeze-drying and lyopreservation of diblock and triblock poly(lactic acid)-poly(ethylene oxide) (PLA-PEO) copolymer nanoparticles.", *Pharm. Dev. Technol.*, 5(4):473-483 (2000).

Delemarre, et al., "Repopulation of macrophages in popliteal lymph nodes of mice after liposome-mediated depletion.", *J. Leukoc. Biol.*, 47(3):251-257 (1990).

Demello and Demello, "Microscale reactors: nanoscale products.", *Lab on a Chip*, 4(2):11N-15N (2004).

Demello, "Control and detection of chemical reactions in microfluidic systems.", *Nature*, 442(7101):394-402 (2006).

Deming, et al., "Facile synthesis of block copolypeptides of defined architecture.", *Nature*, 390(6658):386-389 (1997).

Derfus, et al., "Intracellular Delivery of Quantum Dots for Live Cell Labeling and Organelle Tracking", *Advanced Materials*, 16:961-966 (2004).

Dimarco and Arcamone, "DNA complexing antibiotics: Daunomycin, adriamycin and their derivates.", *Arzneim-forsch. (Drug Res.)*, 25:368-375 (1975).

Ding, et al., "Syntheses of conformationally constricted molecules as potential NAALADase/PSMA inhibitors.", *Org. Lett.*, 6(11):1805-1808 (2004).

Dinkla, et al., "Identification of a streptococcal octapeptide motif involved in acute rheumatic fever.",*J. Biol. Chem.*, 282(26):18686-18693 (2007).

Dykxhoorn, et al., "Killing the messenger: short RNAs that silence gene expression.", *Nat. Rev. Mol. Cell Biol.*, 4(6):457-467 (2003).

Eklund, et al., "Denileukin diftitox: a concise clinical review.", *Expert Rev. Anticancer Ther.*, 5(1):33-38 (2005).

Elbashir, et al., "RNA interference is mediated by 21- and 22-nucleotide RNAs.", *Genes Dev.*, 15(2):188-200 (2001).

Eldridge, et al., "Biodegradable microspheres as a vaccine delivery system," *Mol. Immunol.*, 28(3):287-94 (1991).

Elsässer-Beile, et al., "A new generation of monoclonal and recombinant antibodies against cell-adherent prostate specific membrane antigen for diagnostic and therapeutic targeting of prostate cancer.", *Prostate*, 66(13):1359-1370 (2006).

Farokhzad, et al., "Nanoparticle-Aptamer Bioconjugates: A New Approach for Targeting Prostate Cancer Cells," *Cancer Research*, 64:7668-7672 (2004).

Farokhzad, et al., "Nanoparticle-aptamer bioconjugates for cancer targeting", *Expert Opin. Drug Delivery*, 3(3):311-324 (2006).

Farokhzad, et al., "Targeted nanoparticle-aptamer bioconjugates for cancer chemotherapy in vivo.", *Proc. Natl. Acad. ScI., USA*, 103(16):6315-6320 (2006).

Farr, et al., "The structure of the sinus wall of the lymph node relative to its endocytic properties and transmural cell passage.", *Am. J. Anat.*, 157(3):265-284 (1980).

Fire, et al., "Potent and specific genetic interference by double-stranded RNA in Caenorhabditis elegans.", *Nature*, 391(6669):806-811 (1998).

Fonseca, et al., "Paclitaxel-loaded PLGA nanoparticles: preparation, physicochemical characterization and in vitro anti-tumoral activity.", *J. Control. Release*, 83(2):273-286 (2002).

Fracasso, et al., "Anti-tumor effects of toxins targeted to the prostate specific membrane antigen.", *Prostate*, 53(1):9-23 (2002).

Francis, et al., "A phase I trial of antibody directed enzyme prodrug therapy (ADEPT) in patients with advanced colorectal carcinoma or other CEA producing tumours.", *Br. J. Cancer*, 87(6):600-607 (2002).

Frankel, et al., "Phase I trial of a novel diphtheria toxin/granulocyte macrophage colony-stimulating factor fusion protein (DT388GMCSF) for refractory or relapsed acute myeloid leukemia.", *Clin. Cancer Res.*, 8(5):1004-1013 (2002).

Frederick, et al., "Structural comparison of anticancer drug-DNA complexes: adriamycin and daunomycin.", *Biochemistry*, 29(10):2538-2549 (1990).

Froidevaux, et al., "Somatostatin analogs and radiopeptides in cancer therapy.", *Biopolymers*, 66(3):161-183 (2002).

Fujita, et al., "Cytokine profiling of prostatic fluid from cancerous prostate glands identifies cytokines associated with extent of tumor and inflammation", *The Prostate*, 68(8):872-882 (2008).

Gao, et al., "A method for the generation of combinatorial antibody libraries using pIX phage display," *Proc. Natl. Acad. Sci. U.S.A.*, 99(20): 12612-6 (2002).

Gao, et al., "In vivo cancer targeting and imaging with semiconductor quantum dots.", *Nat. Biotechnol.*, 22(8):969-976 (2004).

Gao, et al., "In vivo molecular and cellular imaging with quantum dots.", *Curr. Op. Biotechnol.*, 16:63-72 (2005).

Gershlick, "Treating atherosclerosis: local drug delivery from laboratory studies to clinical trials," *Atherosclerosis*, 160(2): 259-71 (2002).

Gillies, et al., "An anti-CD20-IL-2 immunocytokine is highly efficacious in a SCID mouse model of established human B lymphoma.", *Blood*, 105(10):3972-3978 (2005).

Grauer, et al., "Identification, purification, and subcellular localization of prostate-specific membrane antigen PSM protein in the LNCaP prostatic carcinoma cell line.", *Cancer Res.*, 58(21):4787-4789 (1998).

Gref, et al., "Biodegradable long-circulating polymeric nanospheres.", *Science*, 263(5153):1600-1603 (1994).

Haensler, et al., "Polyamidoamine cascade polymers mediate efficient transfection of cells in culture", *Bioconjugate Chem.*, 4(5):372-379 (1993).

Haj, et al., "New findings in the study on the intercalation of bisdaunorubicin and its monomeric analogues with naked and nucleus DNA.", *Chem. Biol. Interact.*, 145(3):349-358 (2003).

Hanes, et al., "Polymer microspheres for vaccine delivery.", *Pharm. Biotechnol.*, 6:389-412 (1995).

Hangartner, et al., "Antiviral immune responses in gene-targeted mice expressing the immunoglobulin heavy chain of virus-neutralizing antibodies.", *Proc. Natl. Acad. Sci, USA*, 100:12883-12888 (2003).

Hannon, et al., "Unlocking the potential of the human genome with RNA interference", *Nature*, 431(7006):371-378 (2004).

Harada and Kataoka, "Supramolecular assemblies of block copolymers in aqueous media as nanocontainers relevant to biological applications", *Progress Polymer Sci.*, 31(11):949-982 (2006).

Harper, et al., "Efficacy of a bivalent L1 virus-like particle vaccine in prevention of infection with human papillomavirus types 16 and 18 in young women: a randomised controlled trial.", *Lancet*, 364(9447):1757-1765(2004).

Haseloff and Gerlach, "Simple RNA enzymes with new and highly specific endoribonuclease activities.", *Nature*, 334(6183):585-591 (1988).

Hawiger, et al., "Dendritic cells induce peripheral T cell unresponsiveness under steady state conditions in vivo.", *J. Exp. Med.* 194(6):769-779 (2001).

He, et al., "A microRNA polycistron as a potential human oncogene," *Nature*, 435(7043): 828-833 (2005).

Hélène, "The anti-gene strategy: control of gene expression by triplex-forming-oligonucleotides.", *Anticancer Drug Des.* 6(6):569-584 (1991).

Helene, et al., "Control of gene expression by triple helix-forming oligonucleotides. The antigene strategy.", *Ann, N.Y. Acad. Sci.* 660:27-36 (1992).

Hermann and Patel, "Adaptive recognition by nucleic acid aptamers," *Science*, 287: 820-825 (2000).

Hieda, et al., "Active Immunization Alters the Plasma Nicotine Concentration in Rats", *J. Pharmacol. Exp. Therapeutics*, 283:1076-1081 (1997).

Hieda, et al., "Immunization of rats reduces nicotine distribution to brain", *Psychopharmacology*, 143:150-157 (1999).

(56) References Cited

OTHER PUBLICATIONS

Horoszewicz, et al., "Monoclonal antibodies to a new antigenic marker in epithelial prostatic cells and serum of prostatic cancer patients.", *Anticancer Res.*, 7(56):927-935 (1987).
Houghton, "General method for the rapid solid-phase synthesis of large numbers of peptides: Specificity of antigen-antibody interaction at the level of individual amino acids", *Immunol.*, 82:5131-5135 (1985).
Jackson, et al., "Design and pharmacological activity of phosphinic acid based NAALADase inhibitors.", *J. Med. Chem.*, 44(24):4170-4175 (2001).
Jackson, et al., "Design of NAALADase inhibitors: a novel neuroprotective strategy.", *Curr. Med. Chem.*, 8(8):949-957 (2001).
Johnson and Prud'homme, "Mechanism for rapid self-assembly of block copolymer nanoparticles.", *Phys. Rev. Lett.*, 91(11):118302 (2003).
Jones and Leroux, "Polymeric micelles—a new generation of colloidal drug carriers", *Eur. J. Pharmaceutics Biopharmaceutics*, 48:101-111 (1999).
Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", *Pharmaceutical Research*, 18(3):352-360 (2001).
Junt, et al., "Subcapsular sinus macrophages in lymph nodes clear lymph-borne viruses and present them to antiviral B cells", *Nature*, 450:110-116 (2007).
Kabanov, et al., "DNA Complexes with Polycations for the Delivery of Genetic Material into Cells", *Bioconjugate Chem.*, 6(1):7-20 (1995).
Kamentsky, "Laser scanning cytometry.", *Methods Cell Biol.*, 63:51-87 (2001).
Kanashiro, et al., "Inhibition of mutant p53 expression and growth of DMS-153 small cell lung carcinoma by antagonists of growth hormone-releasing hormone and bombesin.", *Proc. Natl. Acad. Sci., USA*, 100(26):15836-15841 (2003).
Karlin and Altschul, "Applications and statistics for multiple high-scoring segments in molecular sequences.", *Proc. Natl. Acad. Sci. USA*, 90(12):5873-5877 (1993).
Karlin and Altschul, "Methods for assessing the statistical significance of molecular sequence features by using general scoring schemes.", *Proc. Natl Acad Sci. USA*, 87:2264-2268 (1990).
Karrer, et al., "On the key role of secondary lymphoid organs in antiviral immune responses studied in alymphoplastic (aly/aly) and spleenless (Hox11(-)/-) mutant mice.", *J. Exp. Med.*, 185(12):2157-2170 (1997).
Kelly, et al., "The Optical Properties of Metal Nanoparticles: The Influence of Size, Shape, and Dielectric Environment", *J. Phys. Chem. B.*, 107(3):668-677 (2003).
Khademhosseini, et al., "Cell docking inside microwells within reversibly sealed microfluidic channels for fabricating multiphenotype cell arrays," *Lab Chip*, 5(12):1380-6 (2005).
Knight, et al., "Hydrodynamic Focusing on a Silicon Chip: Mixing Nanoliters in Microseconds", *Phys. Rev. Lett.*, 80:3863-3866 (1998).
Köhrer and Rajbhandary, "Proteins carrying one or more unnatural amino acids," In Ibba, et al., (eds.), *Aminoacyl-tRNA Synthetases*, Landes Bioscience, Chapter 31 (2005).
Köhrer, et al., "Complete set of orthogonal 21st aminoacyl-tRNA synthetase-amber, ochre and opal suppressor tRNA pairs: concomitant suppression of three different termination codons in an mRNA in mammalian cells.", *Nucleic Acids Res.*, 32(21):6200-6211 (2004).
Köhrer, et al., "Import of amber and ochre suppressor tRNAs into mammalian cells: a general approach to site-specific insertion of amino acid analogues into proteins.", *Proc. Natl. Acad. Sci., USA*, 98(25):14310-14315 (2001).
Koivunen, et al., "Phage libraries displaying cyclic peptides with different ring sizes: ligand specificities of the RGD-directed integrins.", *Biotechnology (NY)*, 13(3):265-270 (1995).
Koivunen, et al., "Tumor targeting with a selective gelatinase inhibitor", *Nat. Biotechnol.*, 17:768-774 (1999).

Konan, et al., "Preparation and characterization of sterile sub-200 nm meso-tetra(4-hydroxylphenyl)porphyrin-loaded nanoparticles for photodynamic therapy", *Eur. J. Pharmaceutics Biopharmaceutics*, 55:115-124 (2003).
Kozikowski, et al., "Synthesis of urea-based inhibitors as active site probes of glutamate carboxypeptidase II: efficacy as analgesic agents.", *J. Med. Chem.*, 47(7):1729-1738 (2004).
Krieg, et al., "CpG motifs in bacterial DNA trigger direct B-cell activation.", *Nature*, 374(6522):546-549 (1995).
Kreitman, et al., "Efficacy of the anti-CD22 recombinant immunotoxin BL22 in chemotherapy-resistant hairy-cell leukemia.", *N. Engl J. Med.*, 345(4):241-347 (2001).
Kreitman, et al., "Phase I trial of recombinant immunotoxin anti-Tac(Fv)-PE38 (LMB-2) in patients with hematologic malignancies.", *J. Clin. Oncol.*, 18(8):1622-1636 (2000).
Kukowska-Latallo, et al., "Efficient transfer of genetic material into mammalian cells using Starburst polyamidoamine dendrimers", *Proc. Natl. Acad. Sci., USA*, 93(10):4897-4902 (1996).
Kumar, et al., "Inhibition of angiogenesis and tumor growth by SCH221153, a dual alpha(v)beta3 and alpha(v)beta5 integrin receptor antagonist.", *Cancer Res.*, 61(5):2232-2238 (2001).
Kwon, et al., "Pseudopoly(amino acids): A study of the synthesis and characterization of poly(acyl-hydroxyproline-esters)", *Macromolecules*, 22:3250-3255 (1989).
Laakkonen, et al., "Antitumor activity of a homing peptide that targets tumor lymphatics and tumor cells.", *Proc. Natl. Acad. Sci., USA*, 101(25):9381-9386 (2004).
Labhasetwar, et al., "Arterial uptake of biodegradable nanoparticles: Effect of surface modifications ," *J. Pharm. Sci.*, 87(10):1229-34 (1998).
Langer, "Biomaterials in drug delivery and tissue engineering: one laboratory's experience.", *Acc. Chem. Res.*, 33(2):94-101 (2000).
Langer, "New methods of drug delivery," *Science*, 249(4976):1527-33 (1990).
Langer, "Selected advances in drug delivery and tissue engineering", *J. Control. Release*, 62:7-11 (1999).
Langone, et al., "Nicotine and its metabolites. Radioimmunoassays for nicotine and cotinine", *Biochem.*, 12(24):5025-5030 (1973).
Langone & Van Vunakis, "Radioimmunoassay of Nicotine, Cotinine, and □-(3-Pyridyl)-□-oxo-*N*-methylbutyramide", *Met. Enzymol.*, 84:628-640 (1982).
Leamon, et al., "Cytotoxicity of folate-Pseudomonas exotoxin conjugates toward tumor cells. Contribution of translocation domain.", *J. Biol. Chem.*, 268(33):24847-24854 (1993).
Leamon, et al., "Selective targeting of malignant cells with cytotoxin-folate conjugates.", *J. Drug Target.*, 2(2):101-112 (1994).
Leopold, et al., "Fluorescent virions: dynamic tracking of the pathway of adenoviral gene transfer vectors in living cells.", *Human Gene Therapy*, 9(3):367-378 (1998).
Leroy, et al., "Radioimmunodetection of lymph node invasion in prostatic cancer. The use of iodine 123 (123I)-labeled monoclonal anti-prostatic acid phosphatase (PAP) 227 A F(ab')2 antibody fragments in vivo.", *Cancer*, 64(1):1-5 (1989).
Leucuta, et al., "Albumin microspheres as a drug delivery system for epirubicin: pharmaceutical, pharmacokinetic and biological aspects," *International Journal of Pharmaceutics*, 41: 213-7 (1988).
Lim, et al., "A Self-Destroying Polycationic Polymer: Biodegradable Poly(4-hydroxy-l-proline ester)", *J. Am. Chem. Soc.*, 121(24):5633-5639 (1999).
Lim, et al., "Cationic hyperbranched poly(amino ester): a novel class of DNA condensing molecule with cationic surface, biodegradable three-dimensional structure, and tertiary amine groups in the interior.", *J. Am. Chem. Soc*, 123(10):2460-2461 (2001).
Lin, et al., "A microRNA polycistron as a potential human oncogene p828", *Nature*, 435(7043):828-833 (2005).
Lin, et al., "Well-Ordered Mesoporous Silica Nanoparticles as Cell Markers", *Chem. Mater.*, 17:4570-4573 (2005).
Liu, et al., "Cell-Surface labeling and internalization by a fluorescent inhibitor of prostate-specific membrane antigen", *The Prostate*, 68(9):955-964 (2008).
Liu, et al., "Constitutive and antibody-induced internalization of prostate-specific membrane antigen.", *Cancer Res.*, 58(18):4055-4060 (1998).

(56) References Cited

OTHER PUBLICATIONS

Liu, et al., "Folate-targeted enzyme prodrug cancer therapy utilizing penicillin-V amidase and a doxorubicin prodrug.", *J. Drug Target.*, 7:43-53 (1999).

Liu, et al., "Hypermethylation of MCAM gene is associated with advanced tumor stage in prostate cancer", *The Prostate*, 68(4):418-426 (2008).

Liu, et al., "Monoclonal antibodies to the extracellular domain of prostate-specific membrane antigen also react with tumor vascular endothelium.", *Cancer Res.*, 57(17):3629-3634 (1997).

Low, et al., "Folate receptor-targeted drugs for cancer and inflammatory diseases.", *Adv. Drug Deliv. Rev.*, 56(8):1055-1058 (2004).

Lu, et al., "MicroRNA expression profiles classify human cancers", *Nature*, 435(7043):834-838 (2005).

Ludewig, et al., "Induction of optimal anti-viral neutralizing B cell responses by dendritic cells requires transport and release of virus particles in secondary lymphoid organs.", *Eur. J. Immunol.*, 30(1):185-196 (2000).

Lupold, et al., "Identification and characterization of nuclease-stabilized RNA molecules that bind human prostate cancer cells via the prostate-specific membrane antigen.", *Cancer Res.*, 62(14):4029-4033 (2002).

Lyu, et al., "The immunocytokine scFv23/TNF sensitizes HER-2/neu-overexpressing SKBR-3 cells to tumor necrosis factor (INF) via up-regulation of TNF receptor-1.", *Mol. Cancer Ther.*, 4(8):1205-1213 (2005).

Maher, "DNA triple-helix formation: An approach to artificial gene repressors?", *Bioassays* 14:807-815 (1992).

Majer, et al., "Synthesis and biological evaluation of thiol-based inhibitors of glutamate carboxypeptidase II: discovery of an orally active GCP II inhibitor.", *J. Med. Chem.*, 46(10):1989-1996 (2003).

Manolova, et al., "Nanoparticles target distinct dendritic cell populations according to their size", *Eur. J. Immunol.*, 38:1404-1413 (2008).

Manz, et al., "Capillary electrophoresis on a chip", *J. Chromatography*, 593:253-258 (1992).

Mathiowitz, et al., "Polyanhydride Microspheres as Drug Carriers I. Hot Melt Encapsulation", *J. Control. Release*, 5:13-22 (1987).

Mathiowitz, et al., "Novel microcapsules for delivery systems", *Reactive Polymers*, 6:275-283 (1987).

Mathiowitz, et al., "Polyanhydride Microspheres as Drug Carriers. II.Microencapsulation by Solvent Removal", *J. Appl. Polymer Sci.*, 35:755-774 (1988).

Mattheakis, et al., "Optical coding of mammalian cells using semiconductor quantum dots.", *Analytical Biochemistry*, 327(2):200-208 (2004).

Maung, et al., "Probing for a hydrophobic a binding register in prostate-specific membrane antigen with phenylalkylphosphonamidates.", *Bioorg. Med. Chem.*, 12(18):4969-4979 (2004).

McDevitt, et al., "An alpha-particle emitting antibody ([213Bi]J591) for radioimmunotherapy of prostate cancer.", *Cancer Res.*, 60(21):6095-6100 (2000).

McDevitt, et al., "Tumor therapy with targeted atomic nanogenerators.", *Science*, 294(5546):1537-1540 (2001).

Mead, et al., "Laboratory vector competence of black flies (*Diptera:Simuliidae*) for the Indiana serotype of vesicular stomatitis virus.", *Ann. N.Y. Acad. Sci.*, 916:437-443 (2000).

Meister, et al., "Mechanisms of gene silencing by double-stranded RNA.", *Nature*, 431(7006):343-349 (2004).

Melani, et al., "Targeting of interleukin 2 to human ovarian carcinoma by fusion with a single-chain Fv of antifolate receptor antibody.", *Cancer Res.*, 58(18):4146-4154 (1998).

Mempel, et al., "T-cell priming by dendritic cells in lymph nodes occurs in three distinct phases.", *Nature*, 427(6970):154-159 (2004).

Metelitsa, et al., "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", *Blood*, 99(11):4166-4173 (2002).

Meyers, et al., "Development of monoclonal antibody imaging of metastatic prostatic carcinoma.", *Prostate*, 14(3):209-220 (1989).

Milligan and Uhlenbeck, "Synthesis of small RNAs using T7 RNA polymerase," *Methods in Enzymology*, 180: 51-62 (1989).

Moghimi, et al., "Long-circulating and target-specific nanoparticles: theory to practice," *Pharmacol. Rev.*, 53(2): 283-318 (2001).

Mulligan, "The basic science of gene therapy," *Science*, 260(5110):926-32 (1993).

Murphy, et al., "Isolation and characterization of monoclonal antibodies specific for the extracellular domain of prostate specific membrane antigen.", *J. Urol.*, 160(6 Pt 2):2396-2401 (1998).

Murray, et al., "Synthesis and characterization of monodisperse nanocrystals and close-packed nanocrystal assemblies", *Ann. Rev. Mat. Sci.*, 30:545-610 (2000).

Myers and Miller, *CABIOS* (1988).

Nan, et al., "Dual function glutamate-related ligands: discovery of a novel, potent inhibitor of glutamate carboxypeptidase II possessing mGluR3 agonist activity.", *J. Med. Chem.*, 43(5):772-774 (2000).

Neidle, "The molecular basis for the action of some DNA-binding drugs.", *Prog. Med. Chem.*, 16:151-221 (1979).

Nguyen and Wu, "Micromixers—a review.", *J. Micromechan. Microeng.*, 15:R1 (2005).

Notter, et al., "Targeting of a B7-1 (CD80) immunoglobulin G fusion protein to acute myeloid leukemia blasts increases their costimulatory activity for autologous remission T cells.", *Blood*, 97(10):3138-3145 (2001).

Ochsenbein, et al., "Protective T cell-independent antiviral antibody responses are dependent on complement.", *J. Exp. Med.*, 190(8):1165-1174 (1999).

Ochsenbein, et al., "Control of early viral and bacterial distribution and disease by natural antibodies.", *Science*, 286(5447):2156-2159 (1999).

O'Donnell, et al., "c-Myc-regulated microRNAs modulate E2F1 expression," *Nature*, 435(7043): 839-843 (2005).

Okada, et al., "Antigen-engaged B cells undergo chemotaxis toward the T zone and form motile conjugates with helper T cells.", *PLoS Biol.*, 3(6):e150 (2005).

Oliver, et al., "Conformational and SAR analysis of NAALADase and PSMA inhibitors.", *Bioorg. Med. Chem.*, 11(20):4455-4461 (2003).

Pape, et al., "The humoral immune response is initiated in lymph nodes by B cells that acquire soluble antigen directly in the follicles.", *Immunity*, 26(4):491-502 (2007).

Papisov, "Acyclic Polyacetals from Polysaccharides: Biomimetic Biomedical "Stealth" Polymers", *ACS Symposium Series*, 786:301-314 (2001).

Parekh, et al., "Biomarkers for Prostate Cancer Detection", *The Journal of Urology*, 178(6):2252-2259 (2007).

Pasqualini, et al., "Aminopeptidase N is a receptor for tumor-homing peptides and a target for inhibiting angiogenesis.", *Cancer Res.*, 60(3):722-727 (2000).

Patri, et al., "Synthesis and in Vitro Testing of J591 Antibody-Dendrimer Conjugates for Targeted Prostate Cancer Therapy", *Bioconj. Chem.*, 15:1174-1181 (2004).

Pellegrino, et al., "On the development of colloidal nanoparticles towards multifunctional structures and their possible use for biological applications.", *Small*, 1(1):48-63 (2005).

Pfohl, et al., "Trends in microfluidics with complex fluids.", *Chemphyschem*, 4(12):1291-1298 (2003).

Phillips, et al., "Enhanced antibody response to liposome-associated proten antigens: preferential stimulation of IgG2a/b production.", *Vaccine*, 10(3):151-158 (1992).

Porkka, et al., "A fragment of the HMGN2 protein homes to the nuclei of tumor cells and tumor endothelial cells in vivo.", *Proc. Natl. Acad. Sci, USA*, 99(11):7444-7449 (2002).

(56) References Cited

OTHER PUBLICATIONS

Putnam, et al., "Poly(4-hydroxy-I-proline ester): Low-Temperature Polycondensation and Plasmid DNA Complexation", *Macromolecules*, 32(11):3658-3662 (1999).
Qi, et al., "Extrafollicular activation of lymph node B cells by antigen-bearing dendritic cells", *Science*, 312(5780):1672-1676 (2006).
Quintanar-Guerrero, et al., "Preparation Techniques and Mechanisms of Formation of Biodegradable Nanoparticles from Preformed Polymers", *Drug Dev. Industrial Pharmacy*, 24(12):1113-1128 (1998).
Reddy, et al., "Exploiting lymphatic transport and complement activation in nanoparticle vaccines", *Nat. Biotech.*, 25(10):1159-1164 (2007).
Reif, et al., "Balanced responsiveness to chemoattractants from adjacent zones determines B-cell position.", *Nature*, 416(6876):94-99 (2002).
Reiher, et al., "Inhibition of tumor growth by systemic treatment with thrombospondin-1 peptide mimetics.", *Int. J. Cancer*, 98(5):682-689 (2002).
Reubi, et al., "Peptide receptors as molecular targets for cancer diagnosis and therapy.", *Endocr. Rev.*, 24(4):389-427 (2003).
Reynolds, et al., "Rational siRNA design for RNA interference.", *Nat. Biotechnol.*, 22(3):326-330 (2004).
Robbins, et al., "Stable expression of shRNAs in human CD34+ progenitor cells can avoid induction of interferon responses to siRNAs in vitro", *Nature Biotechnology*, 24(5):566-571 (2006).
Robinson, et al., "LEAPT: lectin-directed enzyme-activated prodrug therapy.", *Proc. Natl. Acad. Sci., USA*, 101(40):14527-14532 (2004).
Roost, et al., "Mapping of the dominant neutralizing antigenic site of a virus using infected cells.", *J. Immunol. Methods*, 189(2):233-242 (1996).
Rossbacher and Shlomchik, "The B cell receptor itself can activate complement to provide the complement receptor 1/2 ligand required to enhance B cell immune responses in vivo.", *J. Exp. Med.*, 198(4):591-602 (2003).
Sampson, et al., "Progress report of a Phase I study of the intracerebral microinfusion of a recombinant chimeric protein composed of transforming growth factor (TGF)-alpha and a mutated form of the Pseudomonas exotoxin termed PE-38 (TP-38) for the treatment of malignant brain tumors.", *J. Neurooncol.*, 65(1):27-35 (2003).
Santoyo, et al., "Highly specific and accurate selection of siRNAs for high-throughput functional assays.", *Bioinformatics*, 21(8):1376-1382 (2005).
Sarver, et al., "Ribozymes as potential anti-HIV-1 therapeutic agents.", *Science* 247(4947):1222-1225 (1990).
Schally, et al., "Peptide analogs in the therapy of prostate cancer.", *Prostate*, 45(2):158-166 (2000).
Schultz, "Plasmon resonant particles for biological detection", *Curr. Op. Biotechnol.*, 14:13-22 (2003).
Schultz, et al., "Single-target molecule detection with nonbleaching multicolor optical immunolabels.", *Proc. Natl. Acad. Sci., USA*, 97(3):996-1001(2000).
Shaida, et al., "Expression of BNIP3 correlates with hypoxia-inducible factor (HIF)-1☐, HIF-2☐ and the androgen receptor in prostate cancer and is regulated directly by hypoxia but not androgens in cell lines", *The Prostate*, 68(3):336-343 (2008).
Shen, et al., "Enhanced and prolonged cross-presentation following endosomal escape of exogenous antigens encapsulated in biodegradable nanoparticles", *Immunol.*, 117:78-88 (2006).
Shestopalov, et al., "Multi-step synthesis of nanoparticles performed on millisecond time scale in a microfluidic droplet-based system.", *Lab on a Chip*, 4(4):316-321 (2004).
Shiow, et al., "CD69 acts downstream of interferon-alpha/beta to inhibit S1P1 and lymphocyte egress from lymphoid organs.", *Nature*, 440(7083):540-544 (2006).
Silver, et al., "Prostate-specific membrane antigen expression in normal and malignant human tissues.", *Clin. Cancer Res.*, 3(1):81-85 (1997).

Smith-Jones, et al., "In vitro characterization of radiolabeled monoclonal antibodies specific for the extracellular domain of prostate-specific membrane antigen.", *Cancer Res.*, 60(18):5237-5243 (2000).
Sondel, et al., "Preclinical and clinical development of immunocytokines.", *Curr. Opin. Investig. Drugs*, 4(6):696-700 (2003).
Song, et al., "A Microfluidic System for Controlling Reaction Networks in Time", *Angewandte Chemie—Int'l Ed.*, 42:768-772 (2003).
Spooner, et al., "A novel vascular endothelial growth factor-directed therapy that selectively activates cytotoxic prodrugs.", *Br. J. Cancer*, 88(10):1622-1630 (2003).
Stoermer, et al., "Synthesis and biological evaluation of hydroxamate-Based inhibitors of glutamate carboxypeptidase II.", *Bioorg. Med. Chem. Lett.*, 13(13):2097-2100 (2003).
Storm, et al., "Surface Modification of Nanoparticles to Oppose Uptake by the Mononuclear Phagocyte System", *Adv. Drug Deliv. Rev.*, 17:31-48 (1995).
Stroock, et al., "Chaotic mixer for microchannels.", *Science*, 295(5555):647-651 (2002).
Sutcliffe, et al., "Antibodies that react with predetermined sites on proteins", *Science*, 219:660-666 (1983).
Tang, et al., "In Vitro Gene Delivery by Degraded Polyamidoamine Dendrimers", *Bioconjugate Chem.*, 7:703-714 (1996).
Tang, et al., "Prostate targeting ligands based on N-acetylated alpha-linked acidic dipeptidase.", *Biochem. Biophys. Res. Commun.*, 307(1):8-14 (2003).
Taylor, et al., "Macrophage receptors and immune recognition.", *Annu. Rev. Immunol.*, 23:901-944 (2005).
Tindall, et al., "The Rationale for Inhibiting 5☐-Reductase Isoenzymes in the Prevention and Treatment of Prostate Cancer", *The Journal of Urology*, 179(4):1235-1242 (2008).
Trindade, et al., "Nanocrystalline Semiconductors: Synthesis, Properties, and Perspectives", *Chem. Mat.*, 13(11):3843-3858 (2001).
Tsukamoto, et al., "Phosphonate and phosphinate analogues of N-acylated gamma-glutamylglutamate. potent inhibitors of glutamate carboxypeptidase II.", *Bioorg. Med. Chem. Lett.*, 12(16):2189-2192 (2002).
Uhrich, et al., "Polymeric Systems for Controlled Drug Release", *Chem. Rev.*, 99(11):3181-3198 (1999).
Unkeless, et al., "Structure and function of human and murine receptors for IgG.", *Annu. Rev. Immunol.*, 6:251-281 (1998).
Uwatoku, et al., "Application of Nanoparticle Technology for the Prevention of Restenosis After Balloon Injury in Rats," *Circ. Res.*, 92(7): e62-9 (2003).
Valentini, et al., "Association of anthracycline derivatives with DNA: a fluorescence study.", *Farmaco [Sci]*, 40:377-390 (1985).
Vallabhajosula, et al., "Radioimmunotherapy of prostate cancer in human xenografts using monoclonal antibodies specific to prostate specific membrane antigen (PSMA): studies in nude mice.", *Prostate*, 58(2):145-155 (2004).
Vascotto, et al., "Antigen presentation by B lymphocytes: how receptor signaling directs membrane trafficking.", *Curr., Opin., Immunol.*, 19(1):93-98 (2007).
Vihko, et al., "Radioimaging of Prostatic Carcinoma With Prostatic Acid Phosphatase-Specific Antibodies", *Biotechnology in Diagnostics*, 131-134 (1985).
Von Allmen, et al., "V domain of RAGE interacts with AGEs on prostate carcinoma cells", *The Prostate*, 68(7):748-758 (2008).
Von Andrian and Mempel, "Homing and cellular traffic in lymph nodes.", *Nat. Rev. Immunol.*, 3(11):867-878 (2003).
Wang, et al., "A novel biodegradable gene carrier based on polyphosphoester.", *J. Am. Chem. Soc.*, 123(38):9480-9481 (2001).
Wang, et al., "Autoantibody signatures in prostate cancer.", *N Engl J Med*, 353(12):1224-1235 (2005).
Wang, et al., "Identification of prostate specific membrane antigen (PSMA) as the target of monoclonal antibody 107-1A4 by proteinchip; array, surface-enhanced laser desorption/ionization (SELDI) technology.", *Int. J. Cancer*, 92(6):871-876 (2001).
Wang, et al., "Interactions between an anthracycline antibiotic and DNA: molecular structure of daunomycin complexed to d(CpGpTpApCpG) at 1.2-A resolution.", *Biochemistry*, 26(4):1152-1163(1987).

(56) References Cited

OTHER PUBLICATIONS

Weaver, et al., "Transferrin receptor ligand-targeted toxin conjugate (Tf-CRM107) for therapy of malignant gliomas.", *J. Neurooncol.*, 65(1):3-13 (2003).
Wessels, et al., "Studies of group B streptococcal infection in mice deficient in complement component C3 or C4 demonstrate an essential role for complement in both innate and acquired immunity.", *Proc. Natl. Acad. Sci., USA*, 92(25):11490-11494 (1995).
Whelan, et al., "Efficient recovery of infectious vesicular stomatitis virus entirely from cDNA clones.", *Proc. Natl. Acad. Sci., USA*, 92(18):8388-8392 (1995).
Wilson, et al., "The Structure of an Antigenic Determinant in a Protein", *Cell*, 37:767-778 (1984).
Wind, et al., "An integrated confocal and magnetic resonance microscope for research.", *J. Magn. Reson.*, 147(2):371-377 (2000).
Wlotzka, et al., "In vivo properties of an anti-GnRH Spiegelmer: an example of an oligonucleotide-based therapeutic substance class," *Proc. Natl. Acad. Sci., U. S. A.*, 99(13):8898-902 (2002).
Wright, et al., "Cyclophosphimidelgranulocyte colony-stimulating factor causes selective mobilization of bone marrow hematopoietic stem cells into the blood after M phase of the cell cycle.", *Blood*, 97(8):2278-2285 (2001).
Wu, "Arming antibodies: prospects and challenges for immunoconjugates.", *Nat. Biotechnol.*, 23(9):1137-1146 (2005).
Wu, et al., "Immunofluorescent labeling of cancer marker Her2 and other cellular targets with semiconductor quantum dots.", *Nat. Biotechnol.*, 21(1):41-46 (2003).
Yang, "Imaging of vascular gene therapy.", *Radiology*, 228:36-249 (2003).
Yoo, et al., "In vitro and in vivo anti-tumor activities of nanoparticles based on doxorubicin-PLGA conjugates.", *J. Control. Release*, 68(3):419-431 (2000).
Yuan, et al., "siRNA Selection Server: an automated siRNA oligonucleotide prediction server.", *Nucl. Acids. Res.*, 32:W130-W134 (2004).
Zamore, et al., "RNAi: double-stranded RNA directs the ATP-dependent cleavage of mRNA at 21 to 23 nucleotide intervals.", *Cell*, 101(1):25-33 (2000).
Zauner, et al., "Polylysine-basedtransfection systems utilizing receptor-mediated delivery.", *Adv. Drug Del Rev.*, 30:97-113 (1998).
Zhang, et al., "The proliferative effect of estradiol on human prostate stromal cells is mediated through activation of ERK", *The Prostate*, 68(5):508-516 (2008).
Zheng, et al., "Highly fluorescent, water-soluble, size-tunable gold quantum dots.", *Phys. Rev. Lett.*, 93(7):077402 (2004).
Zhou, et al., "Investigation on a novel core-coated microspheres protein delivery system.", *J. Control. Release*, 75(1-2):27-36 (2001).
Zhou, et al., "Preparation of poly(L-serine ester): a structural analog of conventional poly(L-serine)", *Macromolecules*, 23(14):3399-3406 (1990).
Zuker, "Mfold web server for nucleic acid folding and hybridization prediction", *Nuc. Acid. Res.*, 31:3406-3415 (2003).
Cerchia, et al. "Neutralizing aptamers from whole-cell SELEX inhibit the RET receptor tyrosine kinase", PLoS Biology, 3(4):849-60 (2005).
Foss, et al., "Radiolabeled small-molecule ligands for prostate-specific membrane antigen: in vivo imaging in experimental models of prostate cancer", Clin. Cancer Res., 11:4022-28 (2005).
Govender, et al., "Defining the drug incorporation properties of PLA-PEG nanoparticles", Intl J of Pharmaceutics, 1999:95-110(2000).
Mitra, et al., "Tumour targeted delivery of encapsulated dextran-doxorubicin conjugate using chitosan nanoparticles as carrier", J Controlled Release, 74:317-23 (2001).
Wu, et al., ng-circulation Poly(ethylene glycol)-poly(D,L-lactide) block copolymermicelles with modulated surace chane, J Contl Rel., 77:27-38 (2001).
Zhou, et al., "NAAG peptidase inhibitors and their potential for diagnosis and Therapy", Nature Rev. Drug Disc., 4:1015-26 (2005).
Adams, et al., Amphiphilic block copolymers for drug delivery, J. Pharm. Sol., 92(7):1343-55 (2003).
Astete and Sabliov, "Synthesis and characterization of PLGA nanoparticles", J. Biomat. Sci.,—Polymer Ed., 17:247-289 (2006).
Balenga, et al., "Protective efficiency of dendrosomes as novel nano-sized adjuvants for DNA vaccination against birch pollen allergy", J Biotech., 123(3):602-14 (2006).
Barinka, et al., "Interactions between human glutamate carboxypeptidase II and urea-based inhibitors: Structural characterization", J Med. Chem.,51:7737-43 (2008).
Barinka, et al., "Structural insight into the pharmacophore pocket of human glutamate carboxypoeptidase II", J. Med Chem., 50:3267-73 (2007).
Beck, et al., "A New Long-acting Injectable Microcapsule System for the Administration of Progesterone," Fertil. & Steril., 31(5):545-55 (1979).
Benita, et al., "Characterization of Drug-Loaded Poly(d,/-lactide) Microspheres," J. Pharm. Sci. 73(12):1721-24 (1984).
Caliceti, et al. "Effective protein release from PEG/PLA nano-particles produced by compressed gas anti-solvent precipitation techniques", J of Cont. Release, 94:195-205 (2004).
Ch'ng, et al., "Bioadhesive Polymers as Platforms for Oral Controlled Drug Delivery II: Synthesis and Evaluation of Some Swelling, Water-Insoluble Bioadhesive Polymers," J. Pharm. Sci. 74: 399-405 (1988).
Chandran, et al, "Characterization of a targeted nanoparticle functionalized with a Urea-based inhibitor of prostate-specific membrane antigen (PSMA)", Cancer Biol & Therapy, 7(4):1-9 (2008).
Chen, et al., "Radiohalogenated prostate-specific membrane antigen (PSMA)-based ureas as imaging agents for prostate cancer", J Med Chem., 51(24):7933-43 (2008).
Chickering & Mathiowitz, "Bioadhesive microspheres: I. A novel electrobalance-based method to study adhesive interactions between individual microspheres and intestinal mucosa," J. Control. Release 34:251-62 (1995).
Dancey, et al., "Therapeutic Targets:MTOR an related pathways", Cancer Biol. Ther., 5(9):1065-73 (2006).
Duchene, et al., "Pharmaceutical and Medical Aspects of Bioadhesive Systems for Drug Administration," Drug Development &. Ind. Pharm. 14(2&3):283-31 (1988).
Ewesuedo and Ratain, "Systemically administered drugs", Drug Delivery Systems in Cancer, Humana Press, Chapter 1:3-14 (2004).
Farokhzad, et al., "Cancer nanotechnology: drug encapsulated nanoparticle-aptmer bioconjugates for targeted delivery to prostate cancer cells", 13th Eu. Cancer Conf., Oct. 30-Nov. 3, Paris France (2005).
Gu, et al., "Precise engineering of targeted nanoparticles by using self-assembled biointegrated block copolymers", PNAS, 105(7):2586-91 (2008).
Gurney, et al., "Bioadhesive intraoral release systems: design, testing and analysis," Biomaterials 5:336-40 (1984).
Hamdy, et al., "Co-delivery of cancer-associated antigen and toll-like receptor 4 ligand in PLGA nanoparticles induces potent CD8+ T cell-mediated anti-tumor immunity", Vaccine, 26(39):5046-57 (2008).
Hong, et al., "Enhanced and prolonged cross-presentation following endosomal escape of exogenous antigens encapdulated in biodegradable nanoparticles", Immunol., 117(1):78-88 (2006).
Hotter, et al., "Targeting of a B7-1 (CD80) immunoglobulin G fusion protein to acute myeloid leukemia blasts increases their costimulatory activity for autologous remission T cells." , Blood, 97(10):3138-3145 (2001).
Humblet, et al. "An HPLC/mass spectrometry platform for the development of multimodality contrast agents and targeted therapeutics: prostate-specific membrane antigen small derivatives", Contrast Med. Mol. Imaging, 1:196-211 (2006).
Humblet, et al. "High-affinity near-infrared fluorescent small-molecule contras agents for in vivo imaging of prostate-specific membrane antigen", Molecular Imaging, 4:448-62 (2005).
Igaku, "intracellular trafficking of lipid antigens and their immune recognition by the CD1 system", Exp. Med., 24(7):936-40 (2006).
Illum, "Bioadhesive Microspheres as Potential Nasal Drug Delivery System," Int'l J. Pharm. 39: 189-99 (1987).

(56) References Cited

OTHER PUBLICATIONS

Jiang, et al., "Preparation of PLA and PLGA nanoparticles y binary organic solvent diffusion method", J. Cent. South Univ Technol, 10(3):202-06 (2003).
Kozikowski, et al. "Design of remarkably simple, yet potent urea-based inhibitors of glutamate carboxypeptidase II (NAALADase)", J. Med Chem, 44:298-301 (2001).
Labat-Robert & Decaens, "Glycoproteines du mucus gastrique: structure, fonctions et pathologie," Pathologie Biologie 24:241 (Paris 1979).
Lee, et al. "Adaptations of Nanoscale Viruses and Other Protein Cages for Medical Applications" Nanomedicine—Nanotechnology Biology and Medicine. 2(3):137-149 (2006).
Lehr, et al., "In vitro evaluation of mucoadhesive properties of chitosan and some other natural polymers," International J. Pharmaceutics 78: 43-48 (1992).
Lehr, et al., "Intestinal transit of bioadhesive microspheres in an in situ loop in the rat—a comparative study with copolymers and blends based on poly(acrylic acid)," J. Controlled Rel. 13:51-62 (1990).
Leon-Bay, et al., "Microsphere formation and drug delivery in a series of derivatized amino acids," Winter conference of Medicinal Chemistry (Steamboat Springs, Colarodo 1995).
Maresca, et al., "A series of halogenated heterodirneric inhibitors of prostate specific membrane antigen (PSMA) as radiolabeled probes for targeting prostate cancer", J. Med Chem., 52(2):347-57 (2009).
Martinez-Pomares, et al., "Fc chimeric protein containing the cysteine-rich domain of the murine mannose receptor binds to macrophages from splenic marginal zone and lymph node subcapsular sinus and to germinal centers", J Experimental Med., 184(5):1927-37 (1996).
Mathiowitz, et al., "Morphology of polyanhydride microsphere delivery systems," Scanning Microscopy 4(2):329-340 (1990).
Mease, et al., "N-[N-[(S)-1,3-Dicarboxypropyl]carbamoyl]-4-[18F]fluorobenzyl-L-cysteine, [18F]DCFBC: a new imaging probe for prostate cancer", Clin. Cancer Res., 14(10):3036-43 (2008).
Mikos, et al., "Interaction of Polymer Microspheres with Mucin Gels as a Means of Characterizing Polymer Retention on Mucus," J. Colloid & Interface Sci. 143(2):366-73 (1991).
Misra, et al., "Production of multimeric prostate-specific membrane antigen small-molecule radiotracers using a solid-phase 99mTc preloading strategy", J Nuclear Medicine, 48(8):1379-89 (2007).
Pomper, et al., "New developments in molecular imaging of prostate cancer", Topical Symposium on Advanced Molecular Imaging Techniques in the detection, diagnosis, therapy and follow-up of Cancer, Palazzo Barberini, Rome Dec. 6, 2005.
Pulkkinen, et al., "Three-step tumor of paclitaxel using biotinylated PLA-PEG nanoparticles and avidin-biotin technology: Formulation developing and in vitro anticancer activity", Eur. J Pharm. Biopharm., 70:66-74 (2006).
Raghuvanshi, et al., "Improved immune response from biodegradable polymer particles entrapping tetanus toxoid by use of different immunization protocol and adjuvants", Int J Pharm., 245(1-2):109-21 (2002).
Sapra, et al., "Ligan-targeted liposomal anticancer drugs", Pergamon, Progress in Lipid Research, 42:439-462 (2003).
Scawen, et al., "The Action of Proteolytic Enzymes on the Glycoprotein from Pig Gastric Mucus," Biochemical J. 163:363-68 (1977).
Smart, et al., "An in vitro investigation of mucosa-adhesive materials for use in controlled drug delivery," J. Pharm. & Pharmacol, 36:295-99 (1984).
Spiro, "Glycoproteins," Annual Review of Biochemistry 39:599-638 (Snell, ed. 1970).
Surgery Frontier, "What's new in surgery frontier", 13(3):290-3 (2006).
Sweetman, "Entry for Docetaxel", Martindale:the complete drug reference, 33rd ed., p. 534 (2002).
Tobio, et al.,"Stealth PLA-PEG nanoparticlea as protein carriera for nasal administration", Pharm. Res., 15(2):270-75 (1998).

Walter, et al., "Hydrophillic poly (DL-lactide-co-glycolide) microspheres for the delivery of DNA to human-derived macrophages and dendritic cells", J Control Release, 76(1-2):149-68 (2001).
Yamamoto, et al., "Long-circulation Poly(ethylene glycol)-poly(D,L-lactide) block copolymermicelles with modulated surace chane", J Contl Rel., 77:27-38 (2001).
Yang, et al., "Micelles formed by self-assmbling of polylactide(ethylene glycol) block copolymers in aqueous solutions", J Colloid Interfac Si., 314:470-77 (2007).
Akagi, et al., "Development of vaccine adjuvants using polymeric nanoparticles and their potential applications for anti-HIV vaccine", Yakugaku Zasshi, 127(2):307-17 (2007) English Abstract.
Akagi, et al., "Multifunctional conjugation of proteins on/into bio-nanoparticles prepared by amphiphilic poly(gamma-glutamic acid)", J Biomat Sci Polym Ed., 17(8):875-92 (2006).
Argov-Argaman, et al., "Lactosomes: Structural and compositional classification of unique nanometer-sized protein lipid particles of human milk", J Agric Food Chem., 58:11234-42 (2010).
Avgoustakis, "Pegylated poly(lactide) and poly(lactide-co-glycolide) nanoparticles: preparation, properties and possible applications in drug delivery", Curr Drug Deliv., 1:321-33 (2004).
Chu, et al, "Aptamer:toxin conjugates that specifically target prostate tumor cells", Cancer Res., 66:5989-92 (2006).
Elamanchili, et al., "Pathogen-mimicking nanoparticles for vaccine delivery to dendritic cells", J Cont. Rel., 30(4):378-95 (2007).
Gorelik, et al., "Scanning surface confocal microscopy for simultaneous topographical and fluorescence imaging: application to single virus-like particle entry into a cell", PNAS, 99(26):16018-23 (2002).
Hallahanm, et al., "Integrin-mediated targeting of drug delivery to irradiated tumor blood vessels", Cancer Cell, 3:63-74 (2003).
Harris, et al., "Proteolytic actuation o nanoparticle self-assembly", Angewandte Chemie, 118:3233-7 (2006).
Hennenfent, et al., "Novel formulations of taxanes: a review. Old wine in a new bottle", Ann Oncol., 17:735-49 (2005).
Jayaprakash, et al., "Design and synthesis of a PSMA inhibitor-doxorubicin conjugate for targeted prostate cancer therapy", Chem Med Chem., 1:299-302 (2006).
Kawamura, et al., "Dendritic cells that endocytosed antigen-containing IgG-liposomes elicit effective antitumor immunity", J Immunother., 29(2):165-74 12006).
Koenig, et al., "Immunologic factors in human milk: the effects of gestational age and pasteurization", J Human Lactation, 21:439-43 (2002).
Lamalle-Bernard, et al., "Coadsorption of HIV-1 p24 and gp120 proteins to surfactant-free anionic PLA nanoparticles preserves antigenicity and immunogenicity", J Control Rel., 115(1):57-67 (2006).
Martin, et al., "Crystal structure at 2.8 A of an FcRn/heterodimeric Fc complex: mechanism of pH-dependent binding.", Mol Cell, 7:867-77 (2001).
Matsuo, et al., "Efficient generation of antigen-specific cellular immunity by vaccination with poly(gamma-glutamic acid) nanoparticles entrapping endoplasmic reticulum-targeted peptides", Biochem Biophys Res Commun., 362:1069-72 (2007).
McNeil, "Nanotechnology for the biologist", J Leukoc Biol., 78:575-94 (2005).
Moon, et al., "Engineering Nano- and microparticles to tune immunity", Adv Mater., DOI:10.1002/adma.201200446 (2012).
Oyewumi, et al., "Comparison of cell uptake, biodistribution and tumor retention of folate-coated and PEG-coated gadolinium nanoparticles in tumor-bearing mice", J Control Rel., 93:613-26 (2004).
Oyewumi, et al., "Nano-microparticles as immune adjuvants: correlating particle sizes and the resultant immune responses", Exp Rev Vaccines, 9(9):1095-1107 (2010).
Riley, et al., "Physicochemical evaluation of nanoparticles assembled from Poly(lactic acid)-Poly(ethylene glycol) (PLA_PEG) block copolymers as drug delivery vehicles", Langmuir, 17:3168-74 (2001).
Riley, et al., "Colloidal stability and drug incorporation aspects of micellar-like PLA-PEG nanoparticles", Colloids Surfaces B Biointerfaces, 16:147-59 (1999).

(56) References Cited

OTHER PUBLICATIONS

Shields, et al., "High resolution mapping of the binding site on human IgG1 for Fc gamma RI, Fc gamma RII, Fc gamma RIII, and FcRn and design of IgG1 variants with improved binding to the Fc gamma R", J Biolo Chem., 276(9):6591-6604 (2001).

Shim, "One target different effects: a comparison of distinct therapeutic antibodies against the same targets", Exp Mole Med., 43(10):539-49 (2011).

Suzuki, et al., "Development of effective antigen delivery carrier to dendritic cells via Fc receptor in cancer immunotherapy",Yakugaku Zasshi, 127(2):301-6 (2007). English Abstract.

Taylor, et al., "Development of a specific system for targeting protein to metallophilic macrophages", PNAS, 101(7):1963-8 (2004).

Uto, et al., "Targeting of antigen to dendritic cells with poly(gamma-glutamic acid) nanoparticles induces antigen-specific humoral and cellular immunity", J Immunology, 178(5):2979-86 (2007).

Wakita, et al., "An indispensable role of type-1 IFNs for inducing CTL-mediated complete eradication of established tumor tissue by CpG-liposome co-encapsulated with model tumor antigen", Int. Immunol., 18(3):425-34 (2006).

Yu, et al., "Engineered bio-nanocapsules, the selective vector for drug delivery system", IUBMB Like, 58(1):1-6 (2006).

Akagi, et al., "Preparation and characterization of biodegradable nanoparticles based on poly□gamma-glutamic acid) with L-Phenylalanine as a protein carrier", J Control Release, 108:226-36 (2005).

Akagi, et al., "Protein direct delivery to dendritic cells using nanoparticles based on amphiphilic poly(amino acid) derivatives", Biomaterials, 28:3427-36 (2007).

Bilati, et al., "Development of a nanoprecipitation method intended for the entrapment of hydrophilic drugs into nanoparticles", Eu J Pharma Sci., 24(1):67-75 (2005).

CAS Reg. No. 1069-79-0, 4 pages, Entered STN: Nov. 16, 1984.

Chen, et al., "Beta-arrestin 2 mediates endocytosis of type II TGF-beta receptor and down-regulation of its signaling", Science, 301:1394-7 (2003).

Deng, et al., Optimization of preparative conditions for poly-DL-lactide-polyetyhlene glycol microspheres with entrapped Vibrino Cholera antigens , J Control Release, 58(2):123-31 (1999).

Diwan, et al., "Biodegradable nanoparticle mediated antigen delivery to human cord blood derived dendritic cells for induction of primary T cell responses", J Drug Targeting, 11(8-10):495-507 (2003).

Drug Delivery Systems, 22(3):289 (2007).

Farokhzad, "Nanotechnology for drug delivery: the perfect partnership", Exp Opin Drug Deliv., 5(9):927-9 (2008).

Henrickson, et al., "T cell sensing of antigen dose governs interactive behavior wit dendritic cells and sets a threshold for T cell activation", Nat Immunol., 9(3):282-91 (2008).

Journal of Pediatric Practice, 64(9):1389-94 (2001).

Life Technologies, retrieved from the internet http://www.lifetechnologies.com/us/en/home/references/protocols/nucleic-acid-purification-and-analysis/ma-protocal/agarose-gel-electrophoresis-of-ma.html, retrieved May 30, 2014.

Morein, et al., "Current status and potential application of ISCOMs in veterinary medicine", Adv Drug DelivRev., 56:1367-82 (2004).

Nobs, et al., "Surface modification of poly(lactic acid) nanoparticles by covalent attachment of thiol groups by means of three methods", Intl J Pharma., 250:327-37 (2003).

Ohuchi, et al., "Selection of RNA aptamers against recombinant transforming growth factor-$^2$ type III receptor displayed on cell surface", Biochimie, 88:897-904 (2006).

Olszewski, et al., "NAAG peptidase inhibition reduces locomotor activity and some stereotypes in the PCP model of schizophrenia via group II mGluR", J Neurochem., 89:876-85 (2004).

Ponchel, et al., "Mucoadhesion of colloidal particulate systems in the gastro-intestinal tract", Eu J Pharma Biopharma., 44:25-31 (1997).

Raghavan, et al., "Fc receptors and their interactions with immunoglobulins", Annu Rev Cell Dev.,12:181-220 (1996) Abstract Only.

Ravetch and Bolland, "IgG Fc Receptors", Ann Rev Immunol., 19:275-90 (2001).

Schiffelers, et al., "Cancer siRNA theraphy by tumor selective delivery with ligand-targeted sterically stabilized nanoparticle", Nucleic Acids Res., 32(19):1-10 (2004).

Scholfield, "Composition of soybean lecithin", J Am Oil Sci Soc., 58(10):889-92 (1981).

Shadidi and Sioud, "Selection of peptides for specific delivery of oligonucleotides into cancer cells", Methods Molecular Biol., 252:569-80 (2004).

Singh, et al., "Nanoparticles and microparticles as vaccine-delivery systems", Expert Rev. Vaccines, 6(5):797-808 (2007).

Tamura, et al., "Regulation of Th2 responses by CpG motifs", Respiration, 121(12):1147-55 (2002).

Truong-Le, et al., "Gene transfer by DNA-Gelation nanospheres", Biochem and Biophy., 381:47-55 (1999).

Van de Winkel, et al., "Human IgI Fc receptor heterogeneity: molecular aspects and clinical implications", Immunology Today, 14(5):215-21 (1993).

Wakita, et a.., "Mechanisms for complete eradication of large tumor mass by liposome-CpG nanoparticle tumor vaccine", Clinical Immunology, 45(5):483-90 (2006).

Wei, et al., "Preparation of uniform-sized PELA microspheres with high encapsulation efficiency of antigens by premix membrane emulsification", J Colliod Interface Sol., 323(2):267-73 (2008).

Wu, et al.,"Selection of oligonucleotide apatamers with enhanced uptake and activation of human leukemia B cell", Human Gene, 14:849-60 (2003).

Yamamoto, et al., "Antinociceptive effects of N-acetylaspartylglutamate (NAAG) peptidase inhibitors ZJ-11, ZJ-17 and ZJ-43 in the rat formalin test and in the rat neuropathic pain model", Eur J Neurosci., 20(2):483-94 (2004).

Zhou, et al., "Poly-D,L-lactide-co-poly(ethylene glycol) microspheres as potential vaccine delivery systems", J Control Release, 86:195-205 (2003).

\* cited by examiner

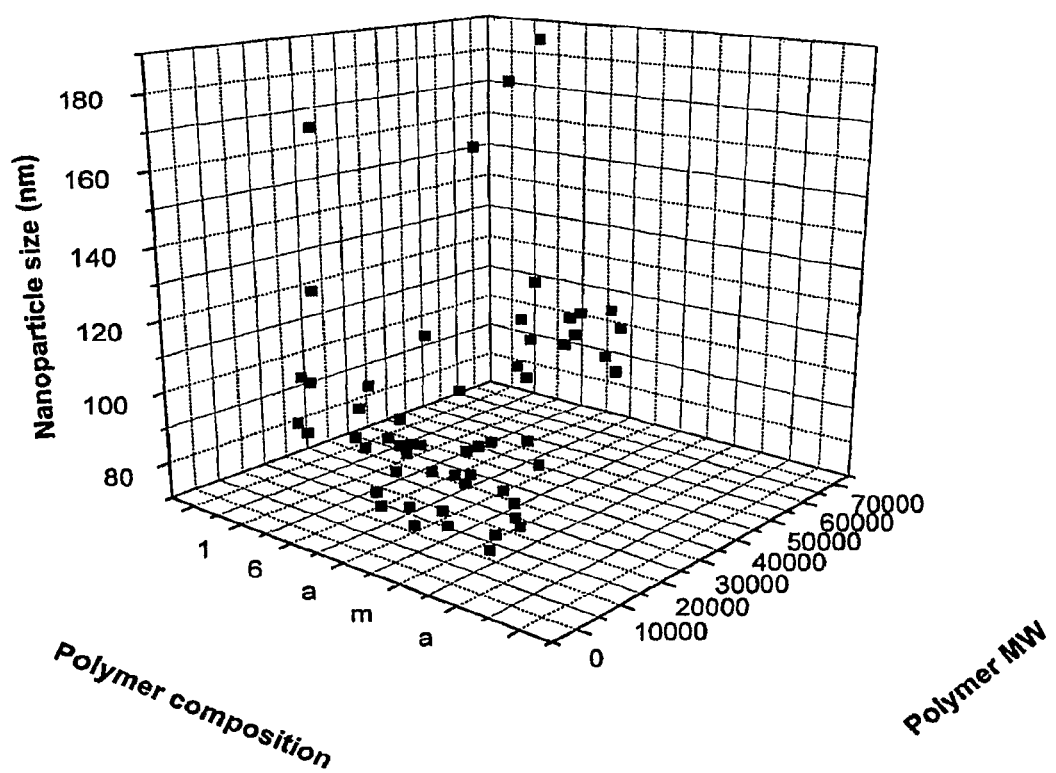
Figure 1: An example of polymer library complexity.

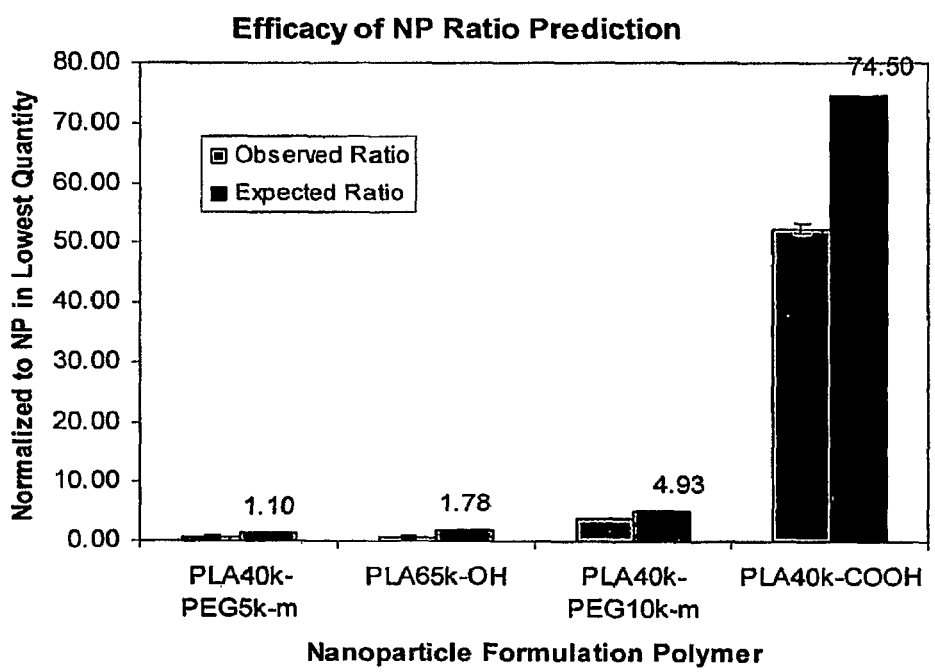

Figure 2: Observed and expected ratios of oligonucleotides. Nanoparticles that were added to the wells were expected to contain a certain quantity of DNA, the relative ratios of which are indicated by the expected ratios. The observed ratio is calculated relative to the lowest oligonucleotide content present, so as to keep numbers greater than one for ease of interpretation.

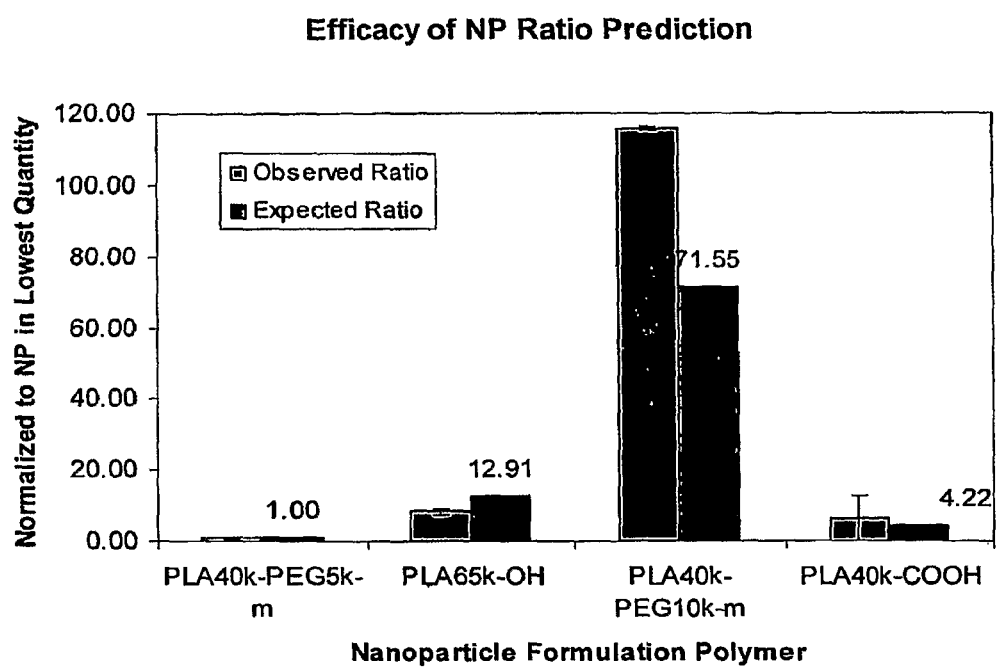
Figure 3: Observed and expected ratios of oligonucleotides. Data was collected similarly to the data presented in *Figure 2*, only different ratios of oligonucleotides are expected since different ratios of particles were incubated together

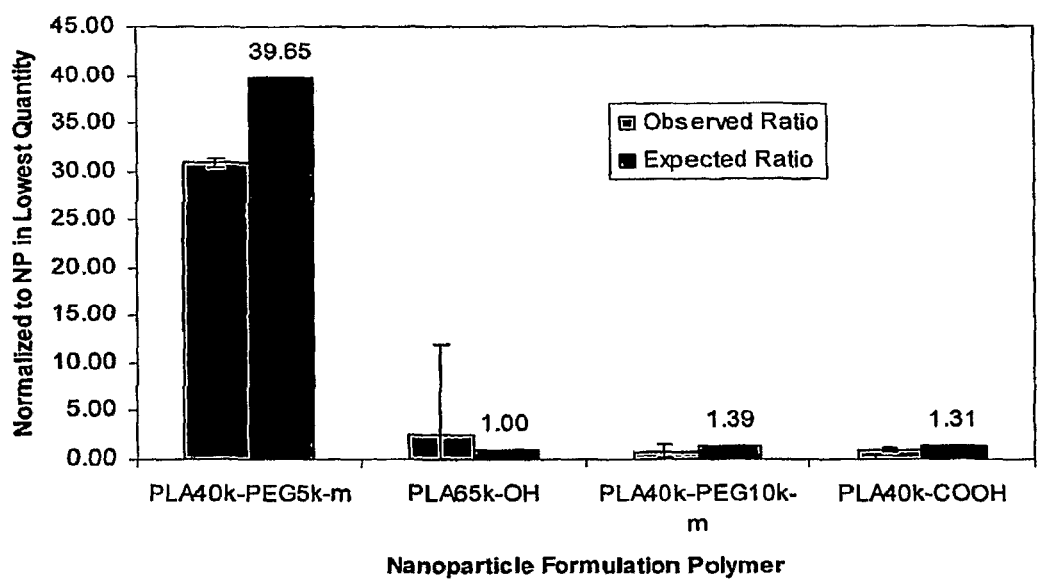
Figures 4: Observed and expected ratios of oligonucleotides. Data was collected similarly to the data presented in *Figures 2-3*, only different ratios of oligonucleotides are expected since different ratios of particles were incubated.

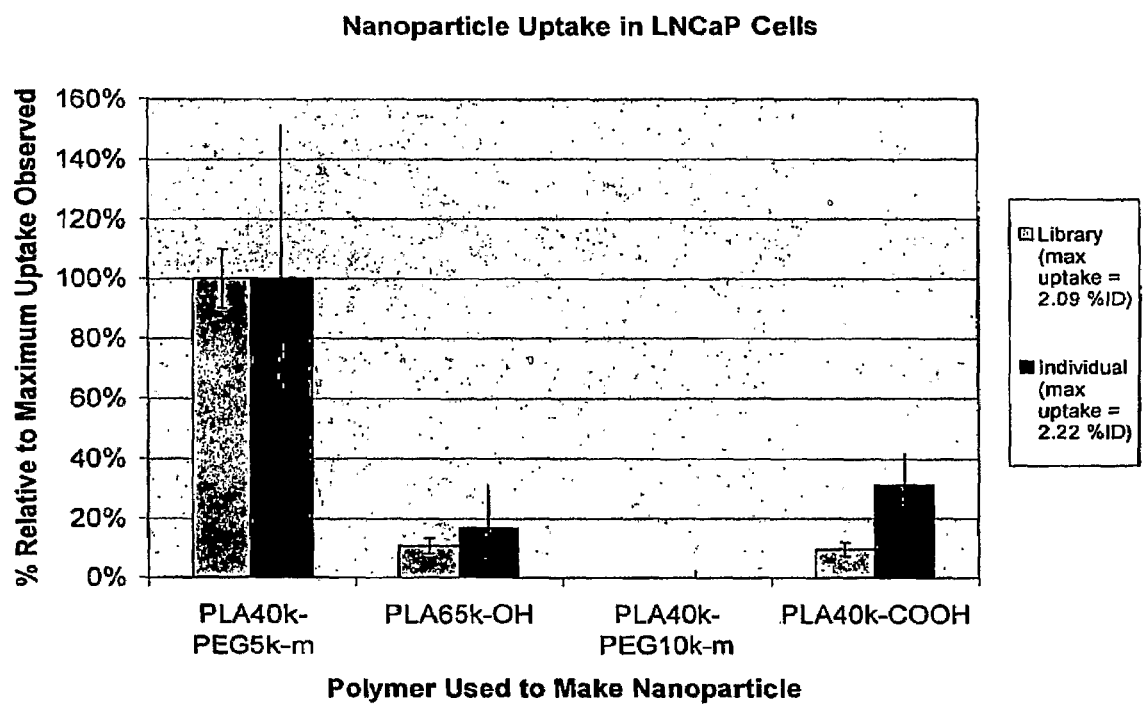

Figure 5: Nanoparticle uptake in LNCaP cells. Whether particles are screened together as a library or separately as individuals against LNCaP cells makes little impact on the results of the screening assay. Results are reported as % relative to maximum uptake observed, in order to normalize for the effects of increased concentration of particles in the "individual" experiments (total concentration of particles in both cases is the same).

SYSTEM FOR SCREENING PARTICLES

RELATED APPLICATIONS

The present application is a U.S. national phase filing under 35 U.S.C. §371 of international PCT application number, PCT/US2006/47975 (published on Jun. 21, 2007 as PCT publication number, WO/2007/070682 A2), filed Dec. 15, 2006 ("the '975 application"), which claims priority under 35 U.S.C. §119(e) to U.S. provisional patent applications, U.S. Ser. No. 60/750,765, filed Dec. 15, 2005 ("the '765 application"), and U.S. Ser. No. 60/747,240, filed May 15, 2006 ("the '240 application"). The entire contents of each of the '975, '765, and '240 applications are incorporated herein by reference.

FIELD OF THE INVENTION

This invention relates to an in vitro and an in vivo system for identifying particles with particular characteristics (e.g., targeting, cellular uptake, drug delivery) from a library of particles.

BACKGROUND OF THE INVENTION

The development of targeted particles for the treatment and detection of human diseases is expected to result in an explosion of the market for this class of biomaterials. In some cases, particles are functionalized with targeted molecules for the specific delivery of particles to a subset of cells, tissues, or organs. The delivery of particles is mediated by specific binding of targeting molecules with distinct chemical moieties that are present on the desired target. This approach has several limitations. First, it requires unique chemical moieties on the cells, tissue, or organ being targeted in order to achieve the desired specificity. And it requires the availability of high affinity targeting molecules that preferentially bind the unique chemical moiety on the cell, tissue, or organ. One problem with this approach is that there are a myriad of potentially useful targets and targeting molecules that have not yet been isolated and/or characterized.

In addition, other biophysiochemical characteristics of the targeted particles frequently need to be optimized in order to make them useful for in vitro or in vivo applications, for example, composition of the particle, surface characteristics, surface charge, and particle size. These many possibilities lead to a very large number of possible particle formulations. Individual evaluation of all these formulations or even a portion of them in vivo would require an equal or larger number of animals. Alternatively, particles could be initially screened using cell-based systems, following which promising formulations could be further evaluated in vivo. However, the results of in vitro evaluations are often not recapitulated by in vivo outcomes. For example, rapid clearance of particles by the liver, spleen, lung, lymphatic system, or bone marrow, the microenvironment of inflammation, or the unique features of tumor microenvironment, e.g., the tumor microvasculature, are not easily reproduced in in vitro models.

Therefore, given these significant drawbacks to current approaches for engineering particles, there remains a need for an efficient system that can be used to identify particles with particular characteristics, including targeting, cell uptake, pharmacokinetics, clinical efficacy, and so forth.

SUMMARY OF THE INVENTION

The present invention provides a system for identifying particles or particle compositions with desired characteristics. The system is particularly useful for screening libraries of particles for particular characteristics. The system includes both in vitro and in vivo screening systems. In certain embodiments, the system is performed in a high-throughput screening format. The invention provides methods, compositions, and kits for carrying out the inventive screening of particles.

In one aspect, the invention provides in vivo methods for identifying particles in a library with desired characteristics (e.g., targeting of a particular cell, tissue, or organ). The method includes providing a library comprising a plurality of particle populations that vary in at least one particle characteristic (e.g., targeting moiety, surface charge, surface hydrophilicity); administering the library to an animal under conditions in which the particles can migrate to a tissue of interest; and recovering a first plurality of particles that have migrated to the cells, tissue, or organ of interest. The at least one characteristic that may vary among particle populations may be particle composition, particle size, surface chemistry, presence or absence of a targeting agent at the surface of the particle, a density of targeting agents conjugated to the surface, the population of targeting agents attached to the particle, etc. The targeting agent can be an oligonucleotide (e.g., aptamer), an oligopeptide, a protein, a glycoprotein, a carbohydrate, a lipid, a small molecule, a metal, or an organometallic complex. In certain embodiments, the targeting agent is an aptamer. In certain particular embodiments, the particles have attached to their surface a plurality of different aptamers (e.g., 2, 3, 4, 5, 10, 20, 50, 100, or more different aptamers). The particles in the library being screened may differ in the population of targeting agents on their surfaces.

The method may further comprise characterizing the recovered particles, for example, determining the identity of the targeting agent(s) attached to the surface of the particles. Each particle population may be characterized by an analytical signature provided by at least one label. The label may include a luminescent agent, a fluorophore, a radionuclide, a small molecule, a polynucleotide, a polypeptide, a semiconductor particle, a magnetic material, a polymer, an ultrasound contrast agent, an MRI contrast agent, or an x-ray contrast agent. The at least one label may be disposed on the surface of the particle, in the interior of the particle, or both. The method may further include identifying at least one characteristic of the first plurality of particles by characterizing the analytical signature of at least a portion of the first plurality of particles. Identifying may include separating at least one label from its respective particle or particles, and identifying the label. In certain embodiments, the label is identified while attached to the particle. The label may also function as a targeting agent (e.g., a nucleic acid aptamer).

The method may further include recovering a second plurality of particles that have migrated to a non-targeted cell, organ, or tissue. Characterizing particles that have migrated to a non-targeted cell, organ, or tissue allows for negative selection of particles with these characteristics. The method may include identifying at least one characteristic of the first plurality of particles (which migrated to the cell, tissue, or organ of interest), identifying at least one characteristic of the second plurality of particles (which migrated to a non-targeted cell, tissue, or organ), preparing an enriched population of particles having many of the same characteristics of the particles that made up the first plurality of particles and fewer or none of the characteristics of the second plurality of particles, and administering the enriched library and recovering particles from the enriched population that migrated to the cells, organ, or tissue of interest. Again, particles may also be recovered from a non-targeted cell, organ, or tissue for negative selection purposes.

The method optionally includes further enriching a library of particles; administering the doubly enriched library; and recovering particles. This iterative process provides for selecting a particle with high specificity for targeting the tissue, cell, or organ of interest. The characteristic that is selected for may be the targeting agent(s) of the particles. In certain embodiments, the aptamers on the surface of the particle are selected for ones that target the tissue, cell, or organ of interest. The aptamers may include a collection of different aptamers. The particles may be microparticles, nanoparticles, or picoparticles. In certain embodiments, the particles are polymeric microparticles, nanoparticles, or picoparticles with an aptamer or plurality of aptamers as the targeting agent. The resulting particles may target a specific organ (e.g., heart, liver, brain, etc.), a specific tissue (e.g., cancer, atherosclerotic plaque, etc.), or a specific cell (e.g., endothelial cell, blood cell, epithelial cell, etc.)

In another aspect, the invention provides in vivo methods for identifying particles with a desired characteristic. The method includes providing a library comprising a plurality of particle populations that vary in at least one particle characteristic, wherein each of the particle populations includes a targeting agent or plurality of targeting agents conjugated to the surface of the particles; administering the library of particles to an animal under conditions in which the particles can migrate to a tissue of interest; and recovering a first plurality of particles that have migrated to the tissue of interest. The characteristic of the particle may be particle composition, particle size, surface chemistry, density of the targeting agents on the surface of the particles, etc.

The method may further include identifying at least one characteristic of the first plurality of particles. Each particle population may be characterized by an analytical signature provided by at least one label. The at least one label may be disposed on the surface of the particle, in the interior portion of the particle, or both. The method may further include identifying at least one characteristic of the first plurality of particles by characterizing the analytical signal of at least a portion of the first plurality of particles. Identifying may include separating at least one label from its respective particle or particles, and identifying the label. In certain embodiments, the label is not separated from the particle in order to be identified.

The method may further include recovering a second plurality of particles that have migrated to a non-targeted tissue. Such particles can provide for negative selection (i.e., characteristics of these particles would be removed or lessened in any enriched library of particles). The method may further include identifying at least one characteristic of the first plurality of particles, identifying at least one characteristic of the second plurality of particles, preparing an enriched library of particles having characteristics of the first plurality of particles and none or fewer of the characteristics from the second plurality or particles; administering the enriched library; and recovering a plurality of the enriched particles from a tissue of interest. The method may further include enriching the recovered plurality of particles and administering a further enriched library and recovering a plurality of the enriched particles from a targeted cell, tissue, or organ.

In certain aspect, the in vitro and in vivo methods are combined. For example, particles are designed first using the in vitro method and then using the in vivo method.

In another aspect, the invention is a population of particles having the characteristics of the first plurality of particles identified by any of the above methods. In another embodiment, the invention provides a population of enriched particles prepared by any of the above methods.

In another aspect, the invention is an in vitro method of screening for particles with a desired characteristic. The method includes providing a library comprising a plurality of particle populations that are each characterized by an analytical signature provided by at least one label, wherein each population comprises a plurality of particles having substantially the same analytical signature; incubating a population of cells with the library for a predetermined period of time under conditions where the cells can take up the particles, wherein the particles include a substance that is necessary to the survival or growth of the cells; and recovering particles taken up by the living cells. The recovered particles are then characterized. Characteristics of the recovered particles that may be determined include particle composition, particle size, surface chemistry, presence or absence of a targeting agent, density of targeting agents on the surface, and composition of targeting agents on the surface.

The method may further include characterizing the at least one analytical signature present in the living cells and correlating it with the corresponding particle population. The method may further include enriching the corresponding particle population; incubating the enriched particle with cells; and recovering particles in living cells. The method may further include recovering those particles that were not taken up by living cells and identifying at least one characteristic of the recovered particles by determining the analytical signature of at least a portion of the recovered particles. Determining the analytical signature may include separating at least one label from its respective particle or particles, and identifying the label. The method may further include determining the at least one analytical signature present in the living cells and correlating it with the corresponding particle population to identify a population of positively correlated particles, recovering those particles that were not taken up by living cells and identifying at least one characteristic of the recovered particles by characterizing the analytical signature of at least a portion of the recovered particles to identify a population of negatively correlated particles, preparing an enriched library of particles having more of the same characteristics as at least a first predetermined fraction of the positively correlated particles and none or fewer of the characteristics of a second predetermined fraction of the negatively correlated particles, and incubating the enriched particles with cells.

In another aspect, the invention provides another in vivo method of screening for particles with desired characteristics. The method includes providing a first library comprising a plurality of particle populations that vary in at least one particle characteristic, wherein each population comprises a plurality of particles having substantially the same characteristics, and wherein each of the particle populations includes a targeting agent conjugated to the surface of the particles; identifying the targeting agent(s) conjugated to those particle populations from the first library that preferentially accumulate in a predetermined tissue or cell type; providing a second library comprising a plurality of particle populations that vary in at least one particle characteristic selected from composition, size, surface chemistry, and density of a targeting agent on the surface of the particle, wherein each population comprises a plurality of particles having substantially the same characteristics, and identifying the at least one particle characteristic of those particle populations from the second library that preferentially accumulate in a predetermined tissue or cell type.

Identifying the targeting agent or identifying the at least one particle characteristic may include administering the library of particles to an animal under conditions in which the particles can migrate to a tissue of interest and recovering a first plurality of particles that have migrated to the tissue of interest. Identifying the targeting agent or identifying the at least one particle characteristic may include incubating a population of cells with the library for a predetermined period of time under conditions where the cells can take up particles, wherein the particles include a substance that is necessary for the survival or growth of the cells and recovering particles from the living cells. In another aspect, the invention is a population of particles having the at least one particle characteristic identified, wherein the identified targeting agent is conjugated to the particles.

BRIEF DESCRIPTION OF THE DRAWING

FIG. 1 shows the complexity of an exemplary library of nanoparticles that may be optimized using the inventive PICO system.

FIG. 2 demonstrates the efficacy of nanoparticle (NP) ratio prediction. Nanoparticles that were added to the wells were expected to contain a certain quantity of DNA, the relative ratios of which are indicated by the expected ratio. Observed ratios are calculated relative to the lowest oligonucleotide content present, so as to keep numbers greater than one for ease of interpretation.

FIG. 3 demonstrates the efficacy of nanoparticle (NP) ratio prediction. Nanoparticles that were added to the wells were expected to contain a certain quantity of DNA, the relative ratios of which are indicated by the expected ratio. Data was collected similar similarly to the data presented in FIG. 2, only different ratios of oligonucleotides are expected since different ratios of particles were incubated together.

FIG. 4 demonstrates the efficacy of nanoparticle (NP) ratio prediction. Nanoparticles that were added to the wells were expected to contain a certain quantity of DNA, the relative ratios of which are indicated by the expected ratio. Data was collected similarly to the data presented in FIGS. 2-3, only different ratios of oligonucleotides are expected since different ratios of particles were incubated together.

FIG. 5 shows the uptake of nanoparticle in human prostate cancer LNCaP cells. Whether nanoparticles are screened together as a library or separately as individuals against LNCaP cells makes little impact on the results of the screening assay. Results are reported as percentages relative to maximum uptake observed, in order to normalize for the effects of increased concentration of particles in the "individual" experiments (the total concentration of particles in both cases was the same).

DEFINITIONS

"Animal": As used herein, the term "animal" refers to any member of the animal kingdom. In some embodiments, "animal" refers to a human, at any stage of development. In some embodiments, "animal" refers to a non-human animal, at any stage of development. In some embodiments, animals include, but are not limited to, mammals, birds, reptiles, amphibians, fish, and/or worms. In certain embodiments, the non-human animal is a mammal (e.g., a rodent, a mouse, a rat, a rabbit, a monkey, a dog, a cat, a sheep, cattle, a primate, and/or a pig). In some embodiments, an animal may be a transgenic animal, genetically-engineered animal, and/or clone.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, including but not limited to protease and reverse transcriptase inhibitors, fusion inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. In a certain embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant techniques) that are commonly found in nature (e.g., organisms, tissues, cells, or viruses). Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, siRNA, DNA, and RNA.

"Biodegradable": As used herein, "biodegradable" polymers are polymers that degrade (i.e., down to monomeric species or oligomers that can be eliminated or processed by the body) under physiological conditions. In preferred embodiments, the polymers and polymer biodegradation byproducts are biocompatible. Biodegradable polymers are not necessarily hydrolytically degradable and may require enzymatic action to fully degrade. In certain embodiments, the biodegradable polymer is degraded by the endosome.

"Decomposition": As used herein, "decomposition" is the process by which a material is broken down under physiological conditions into components that may be metabolized or eliminated by the body. For example, biodegradable polymers may be degraded to oligomers or monomeric species. The oligomers or monomeric species may then be eliminated by the body. In certain embodiments, the polymer or its degradants are metabolized by the liver. In other embodiments, the polymer or its degradants are eliminated by the kidneys. In other embodiments, the polymer or its degradants are eliminated by the digestive system.

"Endosomal conditions": The phrase "endosomal conditions", as used herein, relates to the range of chemical (e.g., pH, ionic strength) and biochemical (e.g., enzyme concentrations) conditions likely to be encountered within endosomal vesicles. For most endosomal vesicles, the endosomal pH ranges from about 5.0 to 6.5.

"Enrichment": As used herein, the term "enrichment" is used to refer to creating a larger proportion of a material having the same composition as a smaller sample of that material. For example, a selected population of polynucleotides may be enriched to include a large proportion of polynucleotides having substantially the same sequences as the original selected population. It is not necessary that the original population be a part of the enriched population, e.g., the population need not be a template for the production of the enriched population. However, in some instances, that may be the case. For example, a population of particles may be enriched by identifying or selecting a subset of the population and manufacturing a larger population having substantially the same composition.

"Pharmaceutically active agent": As used herein, the term "pharmaceutically active agent" refers collectively to biomolecules, small molecules, and bioactive agents which exert a biological effect upon administration to an animal.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, 2'-methoxyribose, 2'-aminoribose, ribose, 2'-deoxyribose, arabinose, and hexose), or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka, et al., *Proc. Natl. Acad. Sci. USA,* 2002, 99(13):8898, the entire contents of which are incorporated herein by reference.

"Polypeptide", "peptide", or "protein": According to the present invention, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least two sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" is used to refer to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

DETAILED DESCRIPTION OF CERTAIN PREFERRED EMBODIMENTS

The present invention provides a system for screening a library of particles for particles with a desired characteristic. The invention provides both in vivo and in vitro systems for screening libraries of particles. The various screening technologies may be used in combination to select a particle or a population of particles for a specific use. In certain embodiments, the particles are screened for the ability to target a specific cell, tissue, or organ. In other embodiments, the particles are screened for their ability to be taken up by a cell. In yet other embodiments, the particles are screened for their ability to deliver an agent to a cell, tissue, or organ. In other embodiments, the particles are screened for their ability to rescue a cell. In one embodiment, the inventive screening system is used to select microparticles (having a diameter between 1 and 1000 microns), nanoparticles (having a diameter between 1 and 1000 nm), or picoparticles (having a diameter between 1 and 1000 pm) with characteristics suitable for delivering an agent to a cell, tissue, or organ of interest. The technology is referred to as Polyplex Iterative Combinatorial Optimization, or PICO. A library of particles is screened by first introducing a population of different into a biological system in vivo or in vitro. Those particles that are found in the cells, tissue, or organ of interest are identified and a second population of particles is prepared by enriching the particles in characteristics identified in the found particles. The process is repeated until the characteristics of the particles are sufficient for the desired preferential partition of the particles in the cells, tissue, or organ of interest. Different characteristics of the particles may be selected for using different or simultaneous screening series. In another embodiment, the library is screened by incubation with cells in vitro. For example, the particles may deliver a necessary nutrient or biologically active molecule to the cells, which require the molecule for survival and/or growth, and the particles having characteristics that facilitate targeted delivery are identified by characterizing the surviving cells, which took up the particles, or the particles taken up by the cells.

High Throughput Development of Targeted Particles

PICO may be used to optimize the biophysical characteristics of particles for use in the targeted delivery of pharmaceutically active agents, contrast agents, or other medically useful materials. Parameters for optimization may include but are not limited to any of size, polymer composition, surface hydrophilicity, surface charge, and the presence, composition and density of targeting agents on the particle surface. A library of particles in which these or other parameters are varied may be produced using combinatorial techniques. Combinatorial techniques may also be used to provide a unique label for each particle or population of particles.

Composition

Particles for use with PICO may be fabricated from a variety of organic and inorganic materials. In one embodiment, particles are fabricated from biodegradable polymers. In certain embodiments, the particles are fabricated from biocompatible polymers. A variety of biodegradable and/or biocompatible polymers are well known to those skilled in the art. Exemplary synthetic polymers suitable for use with the invention include but are not limited to poly(lactide), poly (glycolide), poly(lactic co-glycolic acid), poly(arylates), poly (anhydrides), poly(hydroxy acids), polyesters, poly(ortho esters), polycarbonates, poly(propylene fumerates), poly(caprolactones), polyamides, polyphosphazenes, polyamino acids, polyethers, polyacetals, polylactides, polyhydroxyalkanoates, polyglycolides, polyketals, polyesteramides, poly (dioxanones), polyhydroxybutyrates, polyhydroxyvalyrates, polycarbonates, polyorthocarbonates, poly(vinyl pyrrolidone), biodegradable polycyanoacrylates, polyalkylene oxalates, polyalkylene succinates, poly(malic acid), poly(methyl vinyl ether), poly(ethylene imine), poly(acrylic acid), poly(maleic anhydride), biodegradable polyurethanes and polysaccharides. In certain embodiment, the particles include polyethylene glycol (PEG). In certain embodiments, the polymer used to make the particles is PEGylated (i.e., conjugated to a polyethylene glycol moiety). U.S. patents that describe the use of polyanhydrides for controlled delivery of substances include U.S. Pat. No. 4,857,311 to Domb and Langer, U.S. Pat. No. 4,888,176 to Langer, et al., and U.S. Pat. No. 4,789,724 to Domb and Langer; each of which is incorporated herein by reference.

Naturally-occurring polymers, such as polysaccharides and proteins, may also be employed. Exemplary polysaccharides include alginate, starches, dextrans, celluloses, chitin, chitosan, hyaluronic acid and its derivatives; exemplary proteins include collagen, albumin, and gelatin. Polysaccharides such as starches, dextrans, and celluloses may be unmodified or may be modified physically or chemically to affect one or more of their properties such as their characteristics in the hydrated state, their solubility, or their half-life in vivo. In certain embodiments, the particles do not include protein.

In other embodiments, the polymer includes polyhydroxy acids such as polylactic acid (PLA), polyglycolic acid (PGA), their copolymers poly(lactic-co-glycolic acid) (PLGA), and mixtures of any of these. In certain embodiments, the particles include poly(lactic-co-glycolic acid) (PLGA). In certain embodiments, the particles include poly(lactic acid). In certain other embodiments, the particles include poly(glycolic acid). These polymers are among the synthetic polymers approved for human clinical use as surgical suture materials and in controlled release devices. They are degraded by hydrolysis to products that can be metabolized and excreted. Furthermore, copolymerization of PLA and PGA offers the advantage of a large spectrum of degradation rates from a few days to several years by simply varying the copolymer ratio of glycolic acid to lactic acid, which is more hydrophobic and less crystalline than PGA and degrades at a slower rate.

Non-biodegradable polymers may also be used to produce particles. Exemplary non-biodegradable, yet biocompatible polymers include polystyrene, polyesters, non-biodegradable polyurethanes, polyureas, poly(vinyl alcohol), polyamides, poly(tetrafluoroethylene), poly(ethylene vinyl acetate), polypropylene, polyacrylate, non-biodegradable polycyanoacrylates, non-biodegradable polyurethanes, polymethacrylate, poly(methyl methacrylate), polyethylene, polypyrrole, polyanilines, polythiophene, and poly(ethylene oxide).

Any of the above polymers may be functionalized with a poly(alkylene glycol), for example, poly(ethylene glycol) (PEG) or poly(propyleneglycol) (PPG), or any other hydrophilic polymer system. Alternatively or in addition, they may have a particular terminal functional group, e.g., poly(lactic acid) modified to have a terminal carboxyl group so that a poly(alkylene glycol) or other material may be attached. Exemplary PEG-functionalized polymers include but are not limited to PEG-functionalized poly(lactic acid), PEG-functionalized poly(lactic-co-glycolic acid), PEG-functionalized poly(caprolactone), PEG-functionalized poly(ortho esters), PEG-functionalized polylysine, and PEG-functionalized poly(ethylene imine). When used in formulations for oral delivery, poly(alkylene glycols) are known to increase the bioavailability of many pharmacologically useful compounds, partly by increasing the gastrointestinal stability of derivatized compounds. For parenterally administered pharmacologically useful compounds, including particle delivery systems, poly(alkylene glycols) are known to increase stability, partly by decreasing opsinization of these compounds, thereby reducing immunogenic clearance, and partly by decreasing non-specific clearance of these compounds by immune cells whose function is to remove foreign material from the body. Poly(alkylene glycols) are chains may be as short as a few hundred Daltons or have a molecular weight of several thousand or more.

Co-polymers, mixtures, and adducts of any of the above modified and unmodified polymers may also be employed. For example, amphiphilic block co-polymers having hydrophobic regions and anionic or otherwise hydrophilic regions may be employed. Block co-polymers having regions that engage in different types of non-covalent or covalent interactions may also be employed. Alternatively or in addition, polymers may be chemically modified to have particular functional groups. For example, polymers may be functionalized with hydroxyl, amine, carboxy, maleimide, thiol, N-hydroxy-succinimide (NHS) esters, or azide groups. These groups may be used to render the polymer hydrophilic or to achieve particular interactions with materials that are used to modify the surface as described below.

One skilled in the art will recognize that the molecular weight and the degree of cross-linking may be adjusted to control the decomposition rate of the polymer. Methods of controlling molecular weight and cross-linking to adjust release rates are well known to those skilled in the art.

Methods of producing polymer particles include emulsions, for example, water/oil/water emulsions, oil/water emulsions, spray-drying, freeze-drying, and other methods known to those skilled in the art. Some exemplary methods are disclosed by U.S. Patent Publications Nos. 20020131951 by Langer, 20040070093 by Mathiowitz, 20050123596 by Kohane, 20020119203 by Wright, 20020142093 by Gibson, 20030082236 by Mathiowitz, and 20040086459 by Ottoboni; each of which is incorporated herein by reference. Exemplary fluorescent particles are disclosed in U.S. Patent Publication No. 20040225037 by Lam, incorporated herein by reference.

Particles may also be produced from non-polymer materials, e.g., metals, ceramics, and semiconductors. For example, where it is desired to provide a contrast or imaging agent to a particular tissue, it may not be necessary to combine a particulate agent with a polymer carrier. Rather, a particulate contrast or imaging agent may be conjugated to the selected targeting agent. For example, the particles may be semiconductor particles or quantum dots. Exemplary semiconductor particle compositions include but are not limited to CdS, CdTe, CdSe, InGaP, GaN, PbSe, PbS, InN, InP, and ZnS. Semiconductor nanoparticles are available from Quantum Dot Corporation, Evident Technologies, and other sources known to those skilled in the art. Exemplary methods of producing semiconductor particles are disclosed in U.S. Pat. Nos. 6,576,291, 6,207,229, 6,319,426, 6,322,901, 6,426,513, 6,607,829, 5,505,928, 5,537,000, 6,225,198, 6,306,736, 6,440,213, 6,743,406, and 6,649,138; each of which is incorporated herein by reference. Ceramic particles may also be prepared by any technique known to those skilled in the art, for example, precipitation, or using the techniques described in U.S. Patent Publications No. 20040180096 by Prasad, 20050063898 by Ja Chisholm, 20020110517 by James, or 20050045031 by Rajagopalan, each of which is incorporated herein by reference, may also be employed. Metal particles may also be employed. Exemplary methods of producing metal particles are known to those skilled in the art. Exemplary methods may be found in U.S. Patent Publications Nos. 20050274225 by Bocarsly, 20050235776 by He, 20050218540 by Sastry, 20040099093 by Harutyunan, 20040009118 by Phillips, and 20030115986 by Pozarnsky, each of which is incorporated herein by reference. Metal particles that can be detected by surface-enhanced Raman spectroscopy are disclosed in U.S. Patent Publication No. 20050272160 to Natan, incorporated herein by reference.

The surface chemistry of the particles may be varied using any technique known to the skilled artisan. Both the surface hydrophilicity and the surface charge may be modified. Some methods for modifying the surface chemistry of polymer particles are discussed above. Silane or thiol molecules may be employed to tether particular functional groups to the surface of polymer or non-polymer particles. For example, hydrophilic (e.g., thiol, hydroxyl, or amine) or hydrophobic (e.g., perfluoro, alkyl, cycloalkyl, aryl, cycloaryl) groups may be tethered to the surface. Acidic or basic groups may be tethered to the surface of the particles to modify their surface charge. Exemplary acidic groups include carboxylic acids, nitrogen-based acids, phosphorus based acids, and sulfur based acids. Exemplary basic groups include amines and other nitrogen containing groups. The pKa of these groups may be controlled by adjusting the environment of the acidic or basic group, for example, by including electron donating or electron withdrawing groups adjacent to the acidic or basic group, or by including the acidic or basic group in a conjugated or non-conjugated ring. Alternatively, particles may be oxidized, for example, using peroxides, permanganates, oxidizing acids, plasma etching, or other oxidizing agents, to increase the density of hydroxyl and other oxygenated groups at their surfaces. Alternatively or in addition, borohydrides, thiosulfates, or other reducing agents may be used to decrease the hydrophilicity of the surface.

Particles may be any size between about 1 nm and about 1000 µm, for example about 1 and about 50 nm, between about 50 and about 100 nm, between about 100 and about 500 nm, between about 500 and about 1000 nm, between about 1 µm and about 10 µm, between about 10 µm and about 100 µm or between about 100 µm and about 1000 µm.

Targeting Agents

Targeting agents may be employed to more precisely direct the particles to a tissue of interest. One skilled in the art will recognize that the tissue of interest need not be healthy tissue but may be a tumor or particular form of damage or disease tissue, such as areas of arteriosclerosis or unstable antheroma plaque in the vasculature. Targeting agents may target any part or component of a tissue. For example, targeting agents may exhibit an affinity for an epitope or antigen on a tumor or other tissue cell, an integrin or other cell-attachment agent, an enzyme receptor, an extracellular matrix material, or a peptide sequence in a particular tissue. Targeting agents may include but are not limited to antibodies and antibody fragments, nucleic acid ligands (e.g., aptamers), oligonucleotides, oligopeptides, polysaccharides, low-density lipoproteins (LDLs), folate, transferrin, asialycoproteins, gp120 envelope protein of the human immunodeficiency virus (HIV), carbohydrates, polysaccharides, enzymatic receptor ligands, sialic acid, glycoprotein, lipid, small molecule, bioactive agent, biomolecule, immunoreactive fragments such as the Fab, Fab', or F(ab')$_2$ fragments, etc. A variety of targeting agents that direct pharmaceutical compositions to particular cells are known in the art (see, for example, Cotton, et al., *Methods Enzym.* 217:618; 1993; incorporated herein by reference). Targeting agents may include any small molecule, bioactive agent, or biomolecule, natural or synthetic, that binds specifically to a cell surface receptor, protein or glycoprotein found at the surface of cells. In one embodiment, the targeting agent is an oligonucleotide sequence including $10^{10}$-$10^{20}$ nucleotides. In certain embodiments, the aptamer includes 5-50 nucleotides, preferably 10-40 nucleotides. In another embodiment, the targeting agent is a naturally occurring carbohydrate molecule or one selected from a library of carbohydrates. Libraries of peptides, carbohydrates, or polynucleotides for use as potential targeting agents may be synthesized using techniques known to those skilled in the art. Various macromolecule libraries may also be purchased from companies such as Invitrogen and Cambridge Peptide.

The targeting agent may be conjugated to the particle by covalent interactions. For example, a polymeric particle may be modified with a carboxylate group, following which an aminated targeting agent, or one that is modified to be aminated, is coupled to the polymer using a coupling reagent such as EDC or DCC. Alternatively, polymers may be modified to have an activated NHS ester which can then be reacted with an amine group on the targeting agent. Other reactive groups that may be employed to couple targeting agents to particles include but are not limited to hydroxyl, amine, carboxyl, maleimide, thiol, NHS ester, azide, and alkyne. Standard coupling reactions may then be used to couple the modified material to a second material having a complementary group (e.g., a carboxyl modified targeting agent coupled to an aminated polymer). Particles fabricated from inorganic materials may be modified to carry any of these groups using self-assembled monolayer forming materials to tether the desired functional group to the surface.

Alternatively, the targeting agents can be attached to the particles directly or indirectly via non-covalent interactions. Non-covalent interactions include but are not limited to the following:

1) Electrostatic Interactions: For example, the particle may have a cationic surface or may be reacted with a cationic polymer, such as poly(lysine) or poly(ethylene imine), to provide a cationic surface. The particle surface can then bind via charge interactions with a negatively charged targeting agent. One end of the targeting agent may be attached to a negatively charged polymer (e.g., a poly(carboxylic acid)) or other negatively charged material or molecule that can interact with the cationic polymer surface without disrupting the binding affinity of the targeting agent.

2) Affinity Interactions: For example, biotin may be attached to the surface of the particle and streptavidin may be attached to the targeting agent, or vice versa. The biotin group and streptavidin may be attached to the particle or to the targeting agent via a linker, such as an alkylene linker or a polyether linker. Biotin and streptavidin bind via affinity interactions, thereby retaining the targeting agent on the particle.

3) Metal Coordination: For example, a polyhistidine may be attached to the targeting agent material, and a nitrilotriacetic acid can be attached to the surface of the particle, or vice versa. A metal, such as $Ni^{+2}$, will chelate the polyhistidine and the nitrilotriacetic acid, thereby binding the targeting agent to the particle.

4) Physical Adsorption: For example, a hydrophobic tail, such as polymethacrylate or an alkyl group having at least about 10 carbons, may be attached to the targeting agent. The hydrophobic tail will adsorb onto the surface of a hydrophobic particle or a hydrophobic coating on a particle, for example, a polyorthoester, polysebacic anhydride, unmodified poly(lactic acid), or polycaprolactone.

5) Host-Guest Interactions: For example, a macrocyclic host, such as cucurbituril or cyclodextrin, may be attached to the particle or the targeting agent, and a guest group, such as an alkyl group, a polyethylene glycol, or a diaminoalkyl group, may be attached to the other. In one embodiment, the host and/or the guest molecule may be attached to the particle or the targeting agent via a linker, such as an alkylene linker or a polyether linker. Where the particle is fabricated from a polymeric material, the host or guest group may be incorporated into the polymer.

6) Hydrogen Bonding Interactions: For example, an oligonucleotide having a particular sequence may be attached to the surface of the particle, and an essentially complementary sequence may be attached to the targeting agent. The targeting agent will then bind to the particle core via complementary base pairing with the oligonucleotide attached to the particle. Two oligonucleotides are essentially complimentary if about 80% of the nucleic acid bases on one oligonucleotide form hydrogen bonds via an oligonucleotide base pairing system, such as Watson-Crick base pairing, reverse Watson-Crick base pairing, Hoogsten base pairing, etc., with nucleic acid bases on the second oligonucleotide. In some embodiments, it is desirable for an oligonucleotide sequence attached to the particle to form at least about 6 complementary base pairs with a complementary oligonucleotide attached to the targeting agent. For example, a poly(cytosine) tag may be attached to the particle and a poly(guanine) tag may be attached to the targeting agent. Where the particle is fabricated form a polymer, the entire polymer may be so modified. Some of the poly-C tags will end up on the surface of the particle, and others will remain in the interior portions of the particle. In another embodiment, polysaccharides may be used as a targeting agent. The hydroxyl groups on sugar residues such as glucose and galactose will hydrogen bond with polar moieties on polymers such as poly(vinyl alcohol).

Labels

In one embodiment, each particle in the library has a unique analytical signature, e.g., a molecular bar code defined by an oligonucleotide, provided by one or more labels. The label may include a pattern of luminescence or radioactive emission, a small molecule, a polynucleotide, a polypeptide, or some combination of these. In one embodiment, the label is a short oligonucleotide, e.g., 10-100 bases, that may be incorporated inside or on the surface of the particle. Quantum dots may also be exploited as labels. For example, the techniques described in U.S. Pat. No. 6,602,671, which is incorporated herein by reference, for using quantum dots for inventory control may be employed. Of course, a quantum dot or other semiconductor particle may serve as its own label. Radioisotopes may also be employed. Exemplary radionuclides may include gamma-emitters, positron-emitters, X-ray emitters, beta emitters, and alpha-emitters and include but are not limited to $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99m}Tc$, $^{14}C$, $^{13}N$, $^{15}O$, $^{32}P$, $^{33}P$, and $^{18}F$. A pattern of luminescence may include one or more of a wavelength, an emission time, and an emission polarization, for example, as discussed in U.S. Pat. No. 6,696,299, incorporated herein by reference. The emission time of various luminescent moieties varies with their decay or relaxation mechanism; indirect decay mechanisms may result in extended phosphorescence of the moiety. Luminescent agents may include materials commonly used as clearing agents, such as gadolinium and europium chelates with DTPA, DTPA-BMA, DOTA and HP-DO3A, which are reviewed in Aime, et al., *Chemical Society Reviews* (1998), 27:19-29. These materials and iron oxide particles, among others, are also used as contrast agents for MRI, which may be used as labels for the particles in certain embodiments. Other ceramic or metal agents that can be used to enhance contrast in x-ray, ultrasound, MRI, or other diagnostic techniques may also be employed The signature may include one or more of these labels. Indeed, different kinds of labels (e.g., luminescent and oligonucleotide labels) may be combined to increase the number of unique signatures, or different types of the same labels (e.g., two luminescent labels with different excitation or emission wavelengths or emission times) may be combined.

Labels may be combined with particles according to any method known to those skilled in the art. In one embodiment, labeling agents are conjugated to the particles in the same manner as described for the conjugation of targeting agents, using silane or thiol tethers, or using other techniques known to those of skill in the art. Reactive chemical groups at the surface of polymer particles may be used to covalently link labels to the surface, and any of the non-covalent interactions described above may be employed as well. Alternatively or in addition, combinatorial methods may be employed. Exemplary combinatorial methods for conjugating materials to microparticles are disclosed in U.S. Provisional Applications Nos. 60/750,711 and 60/652,881, the contents of which are incorporated herein by reference.

Alternatively or in addition, contrast or imaging agents may be encapsulated in polymer particles. A variety of methods of making particles in which active agents are encapsulated are well known to those skilled in the art. For example, a double emulsion technique may be used to combine a polymer and label in particles. Alternatively, particles may be prepared by spray-drying. For example, gadolinium or europium complexes such as those described above or diagnostic contrast agents may be encapsulated in polymer particles.

Any analytical technique known to those skilled in the art may be employed to identify the signatures of recovered particles. Where an oligonucleotide is used, quantitative PCR may be employed to determine the amount of each nucleotide present. High throughput multi-plex ELISA systems such as the Bioplex (Bio-Rad, U.S.A.) may also be used to quantitively determine the molecular signature concentrations. Where luminescence or a radioactive emission is used as the label, Fourier transform techniques may be used to identify the various emitters present in a particular sample. Depending on the number of labels, it may be desirable to use several analytical techniques to completely identify all the particles. For example, it is not necessary that all the labels be detectable using one technique, e.g., luminescence or quantitative PCR. Alternatively or in addition, particles may encapsulate one or more labels, and the label may be released from the particle either during screening or after recovery of the particle from a sample and identified separately from the particle.

High-Throughput Optimization of Particles

A library of particles in which specified parameters are varied may be produced using combinatorial chemistry techniques. The combinatorial techniques are also used to provide a unique label for each particle. One or more parameters such as composition, size, surface chemistry (including surface charge and hydrophilicity), the presence of a targeting agent, a density of one or more targeting agents, and the identity of one or more targeting agents, may be varied. The particles may be screened using either in vivo or in vitro techniques.

In some embodiments, PICO is performed several times to optimize various properties of the particles. For example, substantially identical particles may be used to screen targeting agents. The particle-targeting agent conjugates are administered to an animal or a population of cells. The conjugates recovered from the tissue of interest, or the living cells are enriched. The process is repeated with the enriched conjugates. After several repetitions, e.g., 2-20 iterative rounds, this process provides a population of particle-targeting agent conjugates that are selective for a particular tissue or that are taken up by cells without actually purifying targets or ligands for the tissue in advance. Optimal selection is marked by a plateau in enrichment. The population may include more than one targeting agent. As used herein, the term "selective targeting agents" refers to the targeting agent or agents identified by this embodiment of the PICO process. Other characteristics of the particles, e.g., a density of selective targeting agents on the surface, composition, size, and/or surface chemistry, may then be optimized by further rounds of optimization using the PICO method.

In Vivo Screening

For in vivo screening, the library of particles is administered into a biological system, e.g., dog, rodent, mouse, human, or other animal model. Any class of animal may be used. In one embodiment, the animal is a mammal. In some embodiments, the animal model may be engineered or treated to produce a tumor or other defect. In addition, the choice of animal may be dictated by a variety of factors, such as cost and the suitability of the animal as a model for a particular tumor, disease, or tissue. The composition may be administered by intravenous injection. Alternatively, the composition may be administered by other routes, e.g., intra-arterial, inhalational, intradermal, subcutaneous, oral, nasal, bronchial, ophthalmic, transdermal (topical), transmucosal, peritoneal, rectal, and vaginal routes. In some embodiments, the particles are not only optimized to reach a particular tissue site but for a particular delivery route.

After a defined period of time, the tissue of interest is excised and the particles that are present are identified and/or enriched. In one embodiment, the particles are dissolved to release an encapsulated label, which is used to identify the particles that were present in the tissue. The amount of each particle may also be quantitated. Alternatively or in addition, samples from non-targeted organs (e.g., liver, spleen, lung, bone marrow, lymphatic system) are collected, and the particles are identified. Those particles with undesirable biophysiochemical properties, such as non-specific tissue targeting, may be identified and eliminated from subsequent rounds of enrichment.

Those formulations that demonstrate effective targeting of the desired organ (e.g., a high level of signal from particles recovered from a tumor) while optionally demonstrating a low level of uptake by non-targeted organs may be enriched. Where the only variable among the particles is the identity of a polynucleotide targeting agent (that is, the targeting agent also serves as the label), the particles may be enriched using PCR without first identifying the particles, or quantitative PCR may be used to identify the particles. The screening may be repeated several times, for example, to improve the resolution of the assay. In addition, the strength of the screen may be modified by requiring higher or lower levels of signal from a particular label in order to select the corresponding particle for enrichment.

In Vitro Screening

In in vitro methods, the population of particles is administered to a stable cell line in vitro. For example, the cell line may be stable except for requiring an external nutrient or other material, for example, an antibiotic. The particles may encapsulate the required material, and those cells that are able to take up the particles will survive. As for the in vivo methods, those particles that were taken up may be enriched and the procedure repeated. In some embodiments, it may be desirable to perform a negative selection by removing the living cells and assaying the particles in the vicinity of the dead cells. This may identify those particles that have a low rate of cellular uptake.

In some embodiments, a single particle type is produced with a variety of targeting agents. A single particle may be produced with a combination of several targeting agents to screen the targeting agent combinations. In these embodiments, it is not necessary to identify the targeting agents between rounds of screening. Rather, those particles that were preferentially taken up by the cells may simply be amplified. After screening is complete, the targeting agents may be identified by PCR or other suitable techniques. Thus, the targeting agents serve as the label. In some embodiments, particles are produced with common targeting agents, but the properties of the particles themselves (e.g., composition, surface chemistry and charge, etc,) are varied. The surviving cells may be assayed for the particles' label to identify the particular particle composition and surface characteristics. For example, where an oligonucleotide "molecular bar code"

is employed, PCR or some other nucleic acid assay may be used to identify the label. This allows the particle characteristics to be optimized for preferential targeting. By employing both these techniques, both the biophysiochemical characteristics of the particles and the particular targeting agents employed with the particles may be optimized to maximize preferential binding and reduce non-specific uptake of the particles.

These and other aspects of the present invention will be further appreciated upon consideration of the following Example, which is intended to illustrate certain particular embodiments of the invention but are not intended to limit its scope, as defined by the claims.

EXAMPLE

"DNA Barcodes" in High Throughput Screening of Nanoparticles for Desirable Characteristics A procedure was developed to screen different nanoparticle formulations for desirable characteristics in parallel using cultured cells in vitro. This procedure is based on tagging distinct nanoparticle formulations with unique segments of DNA (i.e., "DNA barcodes"), thereby allowing one to quantitatively trace the amount of each particle type present in a cell or tissue, for example. Nanoparticles were incubated at chosen conditions, purified, dissolved by incubation in a mildly basic (0.01 N NaOH) solution (12 hr, room temperature), and assayed directly for DNA content by multiplex assay using Luminex beads (published U.S. Patent Application 2006/0177850, published Aug. 10, 2006; which is incorporated herein by reference) conjugated with the appropriate complementary DNA sequences, all using a Bioplex platform (published U.S. Patent Application 2005/0123455, published Jun. 9, 2005; which is incorporated herein by reference). This system allows for scale-up of nanoparticle optimization for high throughput screening protocols.

We have previously developed methods of creating complex libraries of particle formulations by varying the identity of the polymers used to create them, starting from poly(D,L-lactic-co-glycolic acid) (PLGA), poly(D,L-lactic acid), and poly(ethylene glycol) (PEG) precursors (FIG. 1) together with cell or tissue targeting agents, including, but not limited to antibodies, aptamers, antibody fragments, peptides, carbohydrates, vitamins, small molecules, or magnetic materials. See U.S. Provisional Patent Application, U.S. Ser. No. 60/747,240, filed May 15, 2006; incorporated herein by reference. As part of a proof-of-concept experiment, we have chosen to screen four distinct formulations of particles, each encapsulating trace amounts of biotinylated DNA oligonucleotides (8.37, 6.76, 4.49, 6.10 parts per million (wt/wt)) which were unique for each particle type. First, to establish the validity of the method, we demonstrated that the relative ratios of particles to one another in a sample could be calculated by quantifying the relative ratios of each type of DNA present (FIGS. 2-4). Nanoparticles were added to wells not containing any cells, dissolved in 0.01 N NaOH solution, and then assayed for the resulting free DNA content. Ratios were arbitrarily normalized to the quantity of the lowest nanoparticle added (based on the expected ratios), for ease of interpretation. By simple inspection, one can see that the observed and expected ratios are generally in agreement.

The method was then applied to screen the four nanoparticle preparations (diameters: 238.7±8.6 nm, 291.3±8.3 nm, 230.3±8.3 nm, 278.2±1.1 nm, zeta potentials: −4.10±1.47 mV, −2.95±0.52 mV, 1.17±5.06 mV, −2.63±1.54 mV, from left to right in FIGS. 2-4, respectively) for their ability to penetrate human prostate cancer (LNCaP) cells by incubating them together (37° C., 5% $CO_2$, 1 µg/µL total NP concentration, 6 well plate format, 20 hr) in two formats: (1) each particle formulation was incubated with cells individually (i.e., one nanoparticle formulation per well in a 6 well plate of cells); (2) a mixture of the four distinct particle types was incubated with the cells together (i.e., four nanoparticle formulations per well in a 6 well plate of cells). After incubation, cells were washed twice with isotonic PBS, treated with trypsin, collected, centrifuged, resuspended in PBS, and then lysed by several rounds of flash freezing in liquid nitrogen and thawing in lukewarm water. Nanoparticles released from the intracellular milieu were dissolved in 0.01 N NaOH, and DNA content was assayed directly. The results show that the two methods are comparable (FIG. 5), suggesting that screening particles as a library in parallel is a viable method to greatly reduce the number of individual experiments that are required for optimization of particles (at least by the size of the library, which in the present embodiment is by a factor of four). By decreasing the number of individual experiments that must be run, the present invention facilitates the high throughput optimization of particles with the desired characteristics.

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for inhibiting the formation, progression, and/or recurrence of adhesions at any of the locations, and/or due to any of the causes discussed herein or known in the art. It is also to be understood that any of the compositions made according to the methods for preparing compositions disclosed herein can be used for inhibiting the formation, progression, and/or recurrence of adhesions at any of the locations, and/or due to any of the causes discussed herein or known in the art. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention (e.g., any derivative of zolpidem, any release-retarding ingredient, any buffering agent, any carbohydrate, any fatty acid, any formulation of zolpidem, any dissolution characteristic, any method of producing a formulation, any dosage regimen, any route or location of administration, any method of use, any purpose for which a composition is administered, etc.), can be excluded from any one or more claims. For example, in certain embodiments of the invention the biologically active agent is not an anti-proliferative agent. For purposes of brevity, all of the embodiments in which one or more elements, features, purposes, or aspects is excluded are not set forth explicitly herein.

What is claimed is:

1. A high throughput, iterative, combinatorial screening method of identifying targeting agents or particle properties providing enhanced uptake of particles into targeted cells in tissue, the method comprising the steps of
providing a plurality of synthetic polymeric particle populations,
wherein the particles of each population have substantially the same composition, size, density, surface chemistry, targeting agent or density of targeting agent bound thereto, wherein the particles of a given particle population differ from the particles of another given particle population by at least one particle characteristic, and
wherein each particle of a given population has at least one detectable label which is different from the detectable label of the particles of another given particle population and is different from the targeting agent;
administering the plurality of particle populations to an animal under conditions in which the particles are taken up by cells of a targeted tissue; and
enriching the uptaken particles by repeating the process with different populations of particles,
each population having at least one different particle characteristic, thereby determining the particle characteristics which enhance uptake of the particles by the cells of the targeted tissue.

2. The method of claim 1, wherein the particles have on the surface thereof a targeting agent selected from the group consisting of an oligonucleotide, a polysaccharide, an antibody, an antibody fragment, a nucleic acid ligand, a lipoprotein, folate, transferrin, an asialycoprotein, an enzymatic receptor ligand, sialic acid, a glycoprotein, a lipid, a small molecule, metal, metal complex, a bioactive agent, and an immunoreactive fragment.

3. The method of claim 1, wherein the detectable label is selected from the group consisting of a luminescent agent, a chemiluminescent agent, a phosphorescent agent, a fluorescent agent, a radionuclide, a small molecule, a mass spectroscopy tag, a polynucleotide, a polypeptide, a semiconductor particle, a magnetic material, an ultrasound contrast agent, an MRI contrast agent, and an x-ray contrast agent.

4. The method of claim 3, wherein the label is disposed on the surface of the particle, in the interior of the particle, or both.

5. The method of claim 1 further comprising the step of recovering particles that have migrated to cells of a non-targeted tissue.

6. The method of claim 1, wherein the particles are selected from the group consisting of microparticles, nanoparticles, and picoparticles.

7. The method of claim 1, wherein the polymer is selected from the group consisting of polyesters, polyamides, polycarbonates, polycarbamates, polyacrylates, polystyrene, polyureas, polyethers, polyamines, polyanhydrides, poly(hydroxyacids), poly(lactic acid), poly(glycolic acid), poly (orthoesters), polyphosphazene, ethylene-vinyl acetate copolymer, polyurethanes, polyacrylates, polymethacrylates, polyacrylonitriles, poly(amidoamine) dendrimers, poly(L-lactide-co-L-lysine), poly(serine ester), poly(4-hydroxy-L-proline ester), maleimide-poly(ethyleneglycol)-block-poly (D,L-lactic acid); COOH-poly(ethyleneglycol)-block-poly (D,L-lactic acid); methoxypoly(ethyleneglycol)-block-poly (D,L-lactic acid); proteins; polysaccharides, PEGylated poly (hydroxy acids), PEGylated poly(orthoesters), poly (caprolactone), PEGylated poly(caprolactone), polylysine, PEGylated polylysine, poly(ethylene imine), PEGylated poly (ethylene imine), and combinations thereof.

8. The method of claim 7, wherein the particles are poly (lactic-co-glycolic acid) (PLGA) particles.

9. The method of claim 1, wherein the particles comprise at least one targeting agent.

10. The method of claim 1, wherein the particles comprise a plurality of targeting agents.

11. The method of claim 1 wherein the particles of each of the given particle populations have a different collection of aptamers conjugated to their surface.

12. The method of claim 1, wherein the particles comprise a poly(hydroxy acid) polymer or copolymer or pegylated poly(hydroxy acid) polymer or copolymer.

* * * * *